United States Patent
Sharaiha

(10) Patent No.: US 10,272,228 B1
(45) Date of Patent: Apr. 30, 2019

(54) EXPANDABLE INTUBATION ASSEMBLIES

(71) Applicant: Aspisafe Solutions Inc., New York, NY (US)

(72) Inventor: Talal Sharaiha, New York, NY (US)

(73) Assignee: ASPISAFE SOLUTIONS INC., New York, NY (US)

( * ) Notice: Subject to any disclaimer, the term of this patent is extended or adjusted under 35 U.S.C. 154(b) by 0 days.

(21) Appl. No.: 15/567,577

(22) PCT Filed: May 15, 2017

(86) PCT No.: PCT/US2017/032711
§ 371 (c)(1),
(2) Date: Oct. 18, 2017

(87) PCT Pub. No.: WO2017/200941
PCT Pub. Date: Nov. 23, 2017

Related U.S. Application Data

(60) Provisional application No. 62/337,670, filed on May 17, 2016.

(51) Int. Cl.
*A61M 31/00* (2006.01)
*A61M 25/10* (2013.01)
*A61J 15/00* (2006.01)

(52) U.S. Cl.
CPC ...... *A61M 25/1011* (2013.01); *A61J 15/0003* (2013.01); *A61J 15/0049* (2013.01)

(58) Field of Classification Search
CPC ............ A61J 15/0049; A61M 16/0488; A61M 25/1002; A61M 25/1006; A61M 16/0475; A61M 16/0477; A61M 16/0486; A61M 16/0465; A61M 16/04; A61M 16/0434; A61M 25/1011; A61M 25/10181; A61M 25/104; A61M 25/10; A61B 2017/22074
See application file for complete search history.

(56) References Cited

U.S. PATENT DOCUMENTS

| | | | |
|---|---|---|---|
| 4,091,816 A | 5/1978 | Elam | |
| 4,637,396 A | 1/1987 | Cook | |
| 5,360,402 A * | 11/1994 | Conway | A61L 29/06 604/915 |
| 5,588,424 A * | 12/1996 | Insler | A61M 16/04 128/207.15 |
| 5,971,954 A * | 10/1999 | Conway | A61L 29/085 604/101.05 |
| 8,876,762 B2 | 11/2014 | Dayan et al. | |
| 2003/0041863 A1 | 3/2003 | Hargis | |
| 2003/0066532 A1 | 4/2003 | Gobel | |
| 2007/0203445 A1* | 8/2007 | Kaye | A61M 1/3653 604/6.16 |
| 2007/0295336 A1* | 12/2007 | Nelson | A61M 16/04 128/207.15 |
| 2008/0188803 A1 | 8/2008 | Jang | |

(Continued)

FOREIGN PATENT DOCUMENTS

| | | |
|---|---|---|
| CN | 103394154 | 11/2013 |
| JP | 09-10219 A | 1/1997 |

(Continued)

*Primary Examiner* — Rebecca E Eisenberg
(74) *Attorney, Agent, or Firm* — Van Court & Aldridge LLP

(57) ABSTRACT

Expandable intubation assemblies and methods for using and making the same are provided.

17 Claims, 21 Drawing Sheets

(56) References Cited

U.S. PATENT DOCUMENTS

| | | |
|---|---|---|
| 2009/0032027 A1 | 2/2009 | McCachren et al. |
| 2009/0062725 A1 | 3/2009 | Goebel |
| 2009/0062771 A1 | 3/2009 | Tarola et al. |
| 2011/0028896 A1 | 2/2011 | Burnside et al. |
| 2011/0218493 A1 | 9/2011 | Miyasaka et al. |
| 2013/0053758 A1 | 2/2013 | Kibbe |
| 2014/0276530 A1* | 9/2014 | Gianotti ............ A61M 25/1002 604/500 |
| 2016/0106939 A1 | 4/2016 | Sharaiha et al. |
| 2017/0333654 A1 | 11/2017 | Göbel |

FOREIGN PATENT DOCUMENTS

| | | |
|---|---|---|
| JP | 2003-527918 A | 9/2003 |
| JP | 4091816 B2 | 5/2008 |
| JP | 2014-124264 A | 7/2014 |
| JP | 2015-501681 A | 1/2015 |
| WO | 98/050101 A1 | 11/1998 |
| WO | 2006/034396 A2 | 3/2006 |

\* cited by examiner

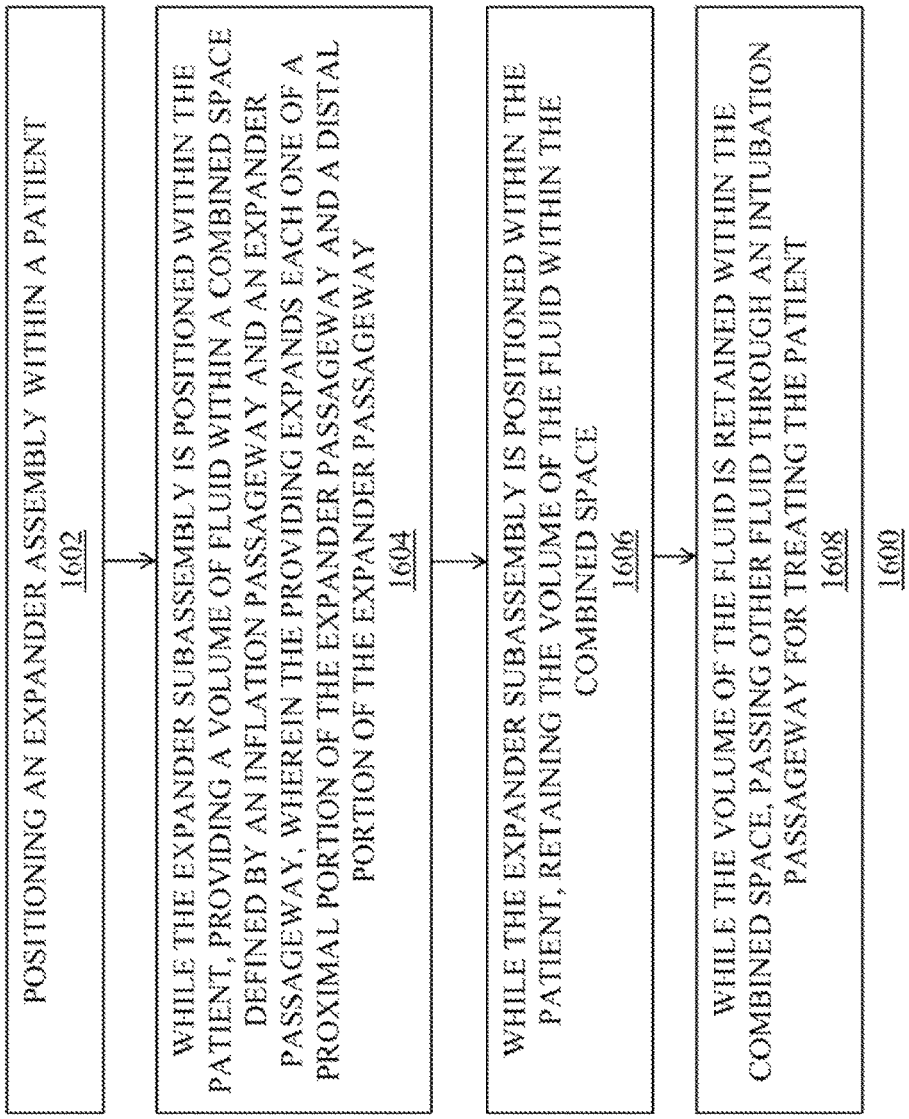

EXPANDABLE INTUBATION ASSEMBLIES

CROSS-REFERENCE TO RELATED APPLICATION(S)

This application is a 371 National Phase entry of International Patent Application No. PCT/US2017/032711 filed May 15, 2017, which claims the benefit of prior filed U.S. Provisional Patent Application No. 62/337,670, filed May 17, 2016, which is hereby incorporated by reference herein in its entirety.

TECHNICAL FIELD

This disclosure relates to expandable assemblies and, more particularly, to expandable intubation assemblies and methods for using and making the same. d methods for using and making the same.

BACKGROUND OF THE DISCLOSURE

Various medical procedures (e.g., intubation procedures) involve a distal end of a tube being inserted into a specific area of a patient and then using the tube for injecting material into the patient and/or for removing material from the patient. However, safely securing such a tube at a particular position within the patient during use has heretofore been infeasible. Moreover, safely preventing certain material from passing along the external surface of such a tube during use has heretofore been infeasible.

SUMMARY OF THE DISCLOSURE

This document describes expandable assemblies and methods for using and making the same.

For example, an intubation assembly may be include a body structure extending from a proximal body end to a distal body end, an intubation passageway extending within the body structure and along at least an intubation portion of the length of the body structure from a proximal intubation passageway opening to a distal intubation passageway opening, an expander subassembly coupled to the body structure for defining an expander passageway between the expander subassembly and the body structure, and an inflation passageway extending along at least an inflation portion of the length of the body structure from a proximal inflation passageway opening to a distal inflation passageway opening, wherein the distal inflation passageway opening fluidly couples the inflation passageway to the expander passageway, the expander subassembly includes a proximal expander subassembly portion defining a proximal portion of the expander passageway between the proximal expander subassembly portion and a proximal portion of the body structure and a distal expander subassembly portion defining a distal portion of the expander passageway between the distal expander subassembly portion and a distal portion of the body structure, the proximal portion of the expander passageway is fluidly coupled to the distal portion of the expander passageway, and, when a volume of fluid is retained within the combined space defined by the inflation passageway and the expander passageway, a portion of the volume of the fluid is transferred from the proximal portion of the expander passageway to the distal portion of the expander passageway when an external force is applied to the proximal expander subassembly portion and the portion of the volume of the fluid is transferred from the distal portion of the expander passageway to the proximal portion of the expander passageway when the external force is removed from the proximal expander subassembly portion.

As another example, a method of intubating a patient with an intubation assembly may be provided, where the assembly may include a body structure, an intubation passageway extending within the body structure and along at least an intubation portion of the length of the body structure from a proximal intubation passageway opening to a distal intubation passageway opening, an expander subassembly coupled to the body structure for defining an expander passageway between the expander subassembly and the body structure, and an inflation passageway extending along at least an inflation portion of the length of the body structure from a proximal inflation passageway opening to a distal inflation passageway opening, wherein the distal inflation passageway opening fluidly couples the inflation passageway to the expander passageway, wherein the expander subassembly includes a proximal expander subassembly portion defining a proximal portion of the expander passageway between the proximal expander subassembly portion and a proximal portion of the body structure and a distal expander subassembly portion defining a distal portion of the expander passageway between the distal expander subassembly portion and a distal portion of the body structure, wherein the distal inflation passageway opening fluidly couples the inflation passageway to the distal portion of the expander passageway, wherein the inflation passageway further includes an intermediate inflation passageway opening that fluidly couples the inflation passageway to the proximal portion of the expander passageway, and wherein the proximal portion of the expander passageway is fluidly coupled to the distal portion of the expander passageway only via the inflation passageway, and wherein the method may include positioning the expander subassembly within the patient and, while the expander subassembly is positioned within the patient, providing a volume of fluid within the combined space defined by the inflation passageway and the expander passageway, wherein the providing expands each one of the proximal portion of the expander passageway and the distal portion of the expander passageway, retaining the volume of the fluid within the combined space, and, while the volume of the fluid is retained within the combined space, passing other fluid through the intubation passageway for treating the patient.

As yet another example, an intubation assembly may include a body structure extending from a proximal body end to a distal body end, an intubation passageway extending within the body structure and along at least an intubation portion of the length of the body structure from a proximal intubation passageway opening to a distal intubation passageway opening, an expander subassembly coupled to the body structure for defining an expander passageway between the expander subassembly and the body structure, an inflation passageway extending along at least an inflation portion of the length of the body structure from a proximal inflation passageway opening to a distal inflation passageway opening, and an auxiliary passageway extending along at least an auxiliary portion of the length of the body structure from a proximal auxiliary passageway opening to a distal auxiliary passageway opening, wherein the distal auxiliary passageway opening is directed along the length of the body structure at least one of towards the expander subassembly and away from the expander subassembly, wherein the distal inflation passageway opening fluidly couples the inflation passageway to the expander passageway, and wherein, when a volume of fluid is retained within the combined space defined by the inflation passageway and the expander passageway, the expander subassembly is operative to remain in an expanded configuration.

This Summary is provided only to summarize some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters may refer to like parts throughout, and in which:

FIG. 16 is a flowchart of an illustrative process for intubating a patient.

DETAILED DESCRIPTION OF THE DISCLOSURE

Figure 1:
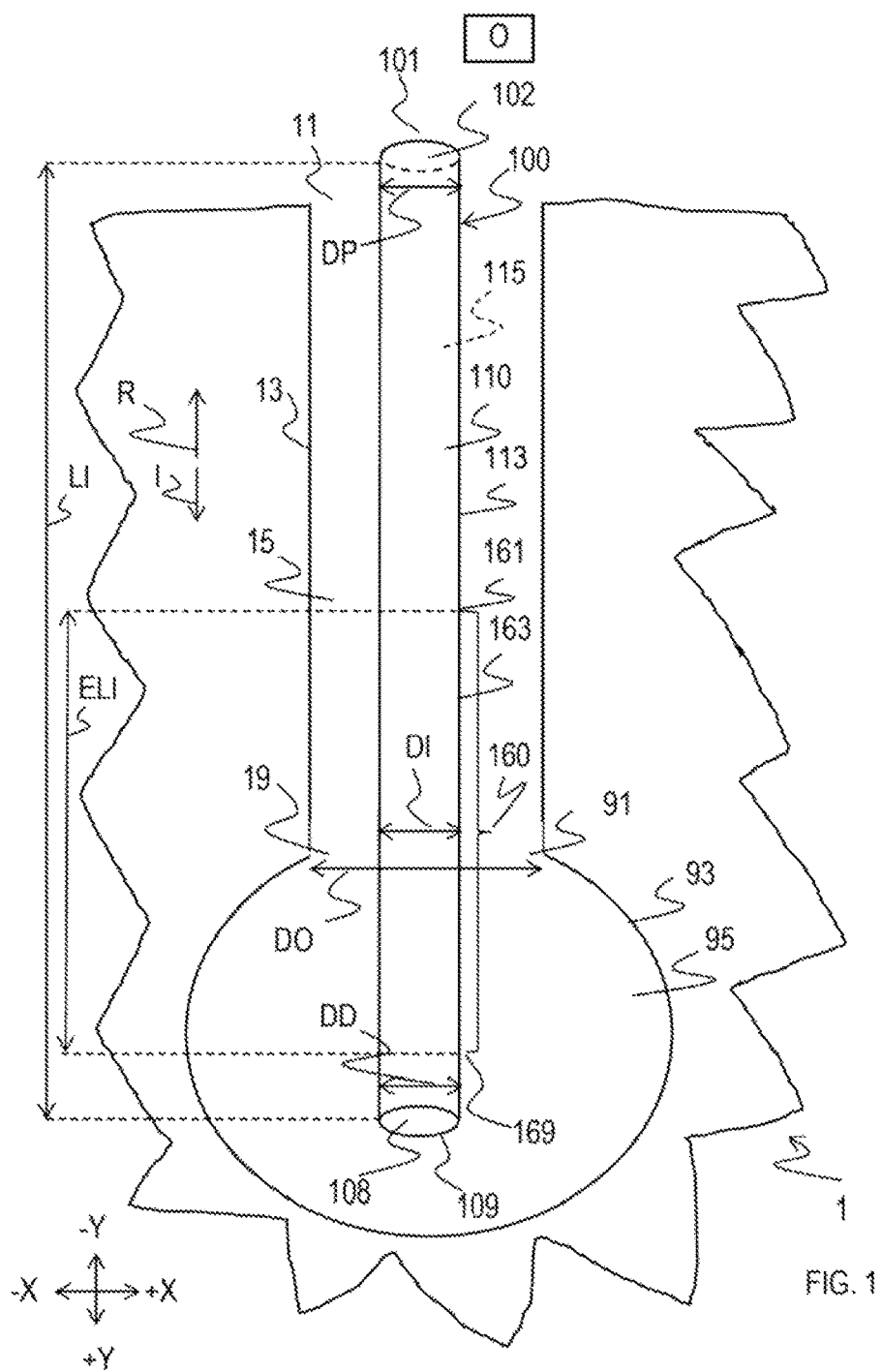
FIG. 1 is a cross-sectional view of a patient with an intubation assembly in an insertion state.
Figure 1A:
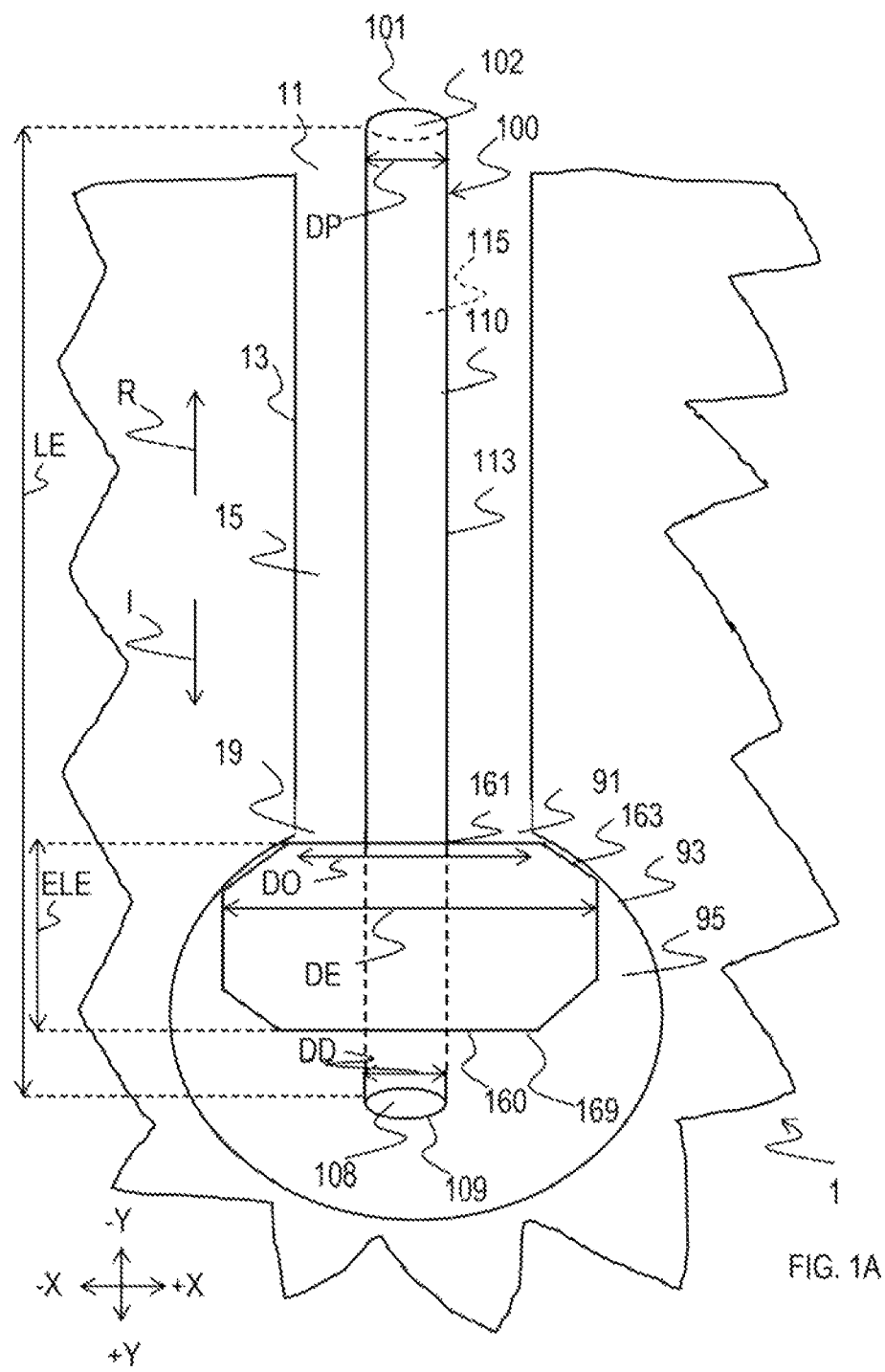
FIGS. 1A-1C are cross-sectional views, similar to FIG. 1, of the patient of FIG. 1 with the intubation assembly of FIG. 1 in various illustrative expanded states.
Figure 1B:
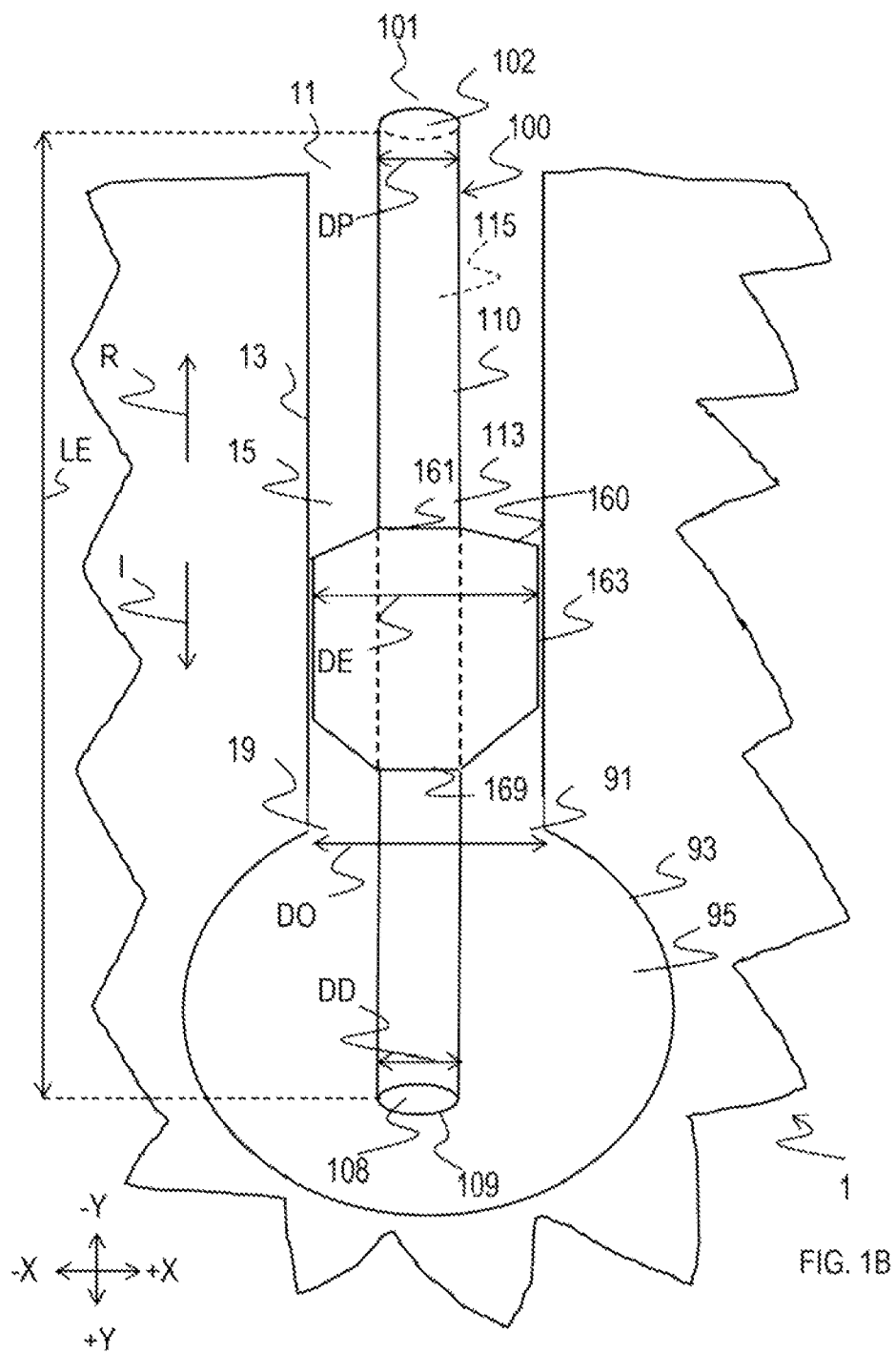
Figure 1C:
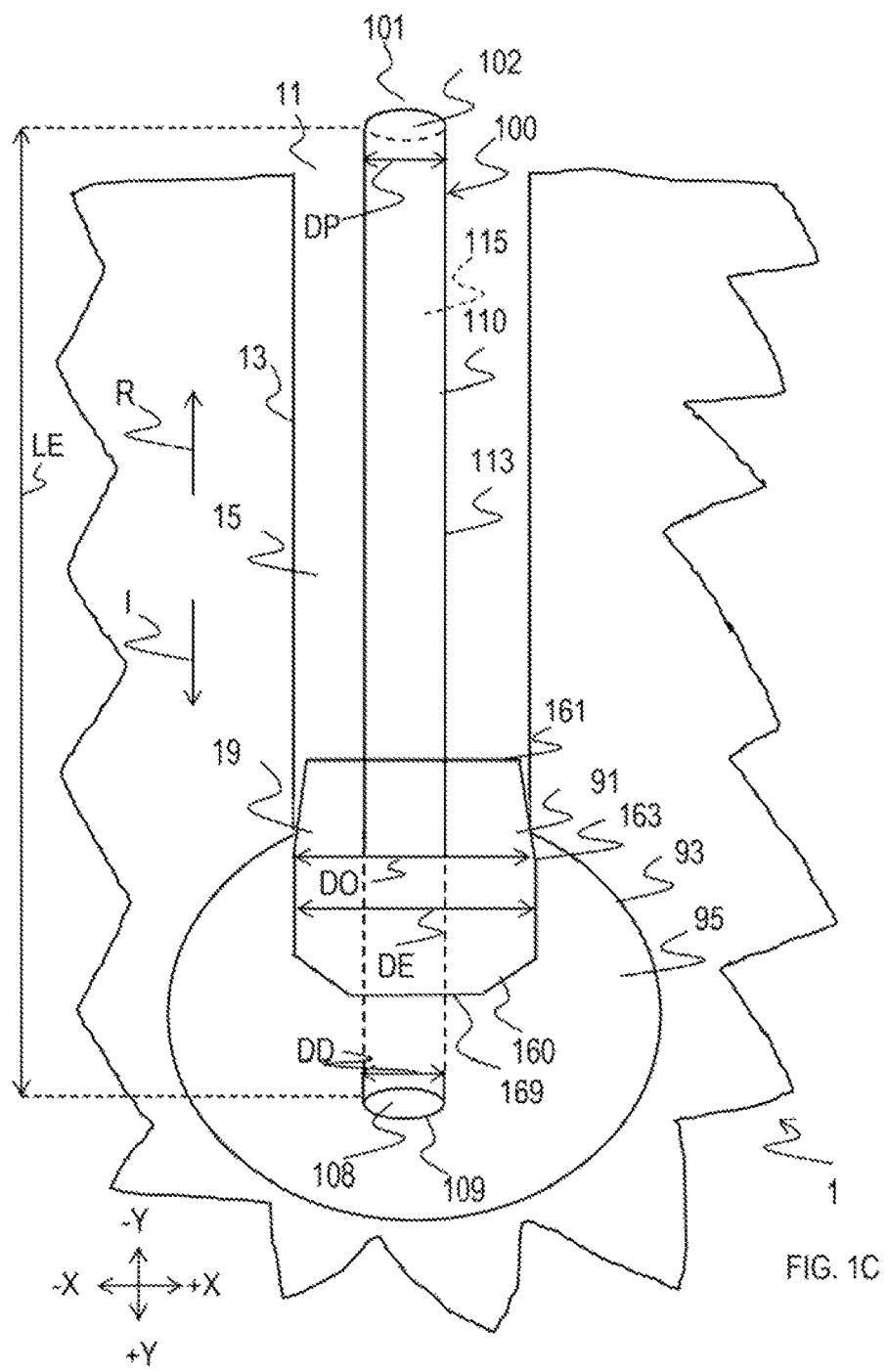
Figure 1D:
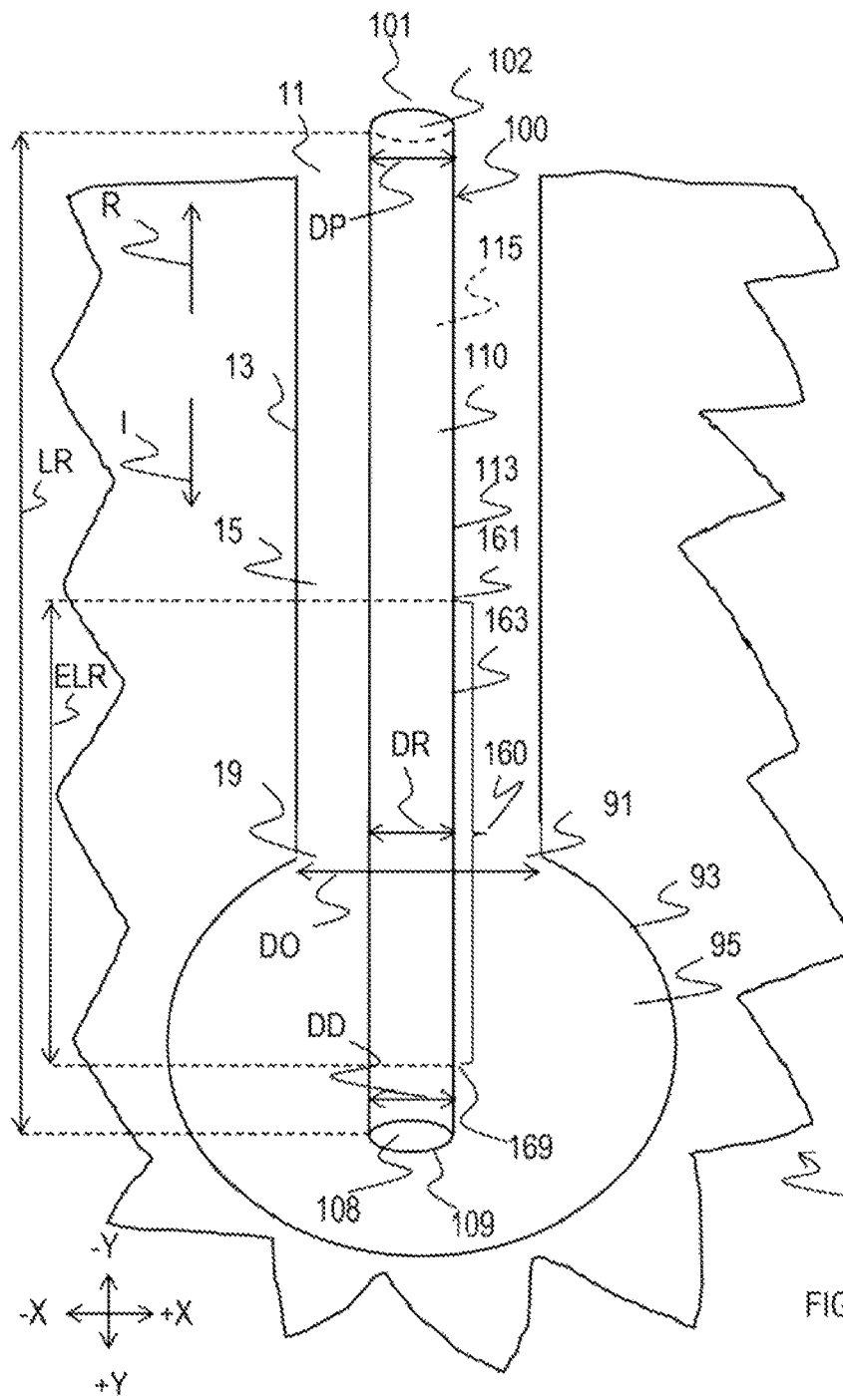
FIG. 1D is a cross-sectional view, similar to FIGS. 1-1C, of the patient of FIGS. 1-1C with the intubation assembly of FIGS. 1-1C in a removal state.

FIGS. 1-1D show an illustrative assembly 100 in various configurations or stages of use with respect to a patient 1. Assembly 100 may be an intubation assembly or any other suitable assembly for use in any suitable procedure with respect to any suitable patient 1. As shown in FIGS. 1-1D, for example, assembly 100 may extend between a proximal or first assembly end 101, which may have an outer cross-sectional dimension (e.g., diameter) DP, and a distal or second assembly end 109, which may have an outer cross-sectional dimension (e.g., diameter) DD. Assembly 100 may include at least one tube or tube subassembly 110 providing a body structure 112 that may extend between ends 101 and 109. Tube subassembly 110 may include at least one tube wall 113 that may define at least one internal or intubation passageway 115 extending within and along at least a portion of assembly 100. Wall 113 may also include at least one proximal or first tube opening 102 that may provide access to passageway 115 (e.g., fluid communication between passageway 115 and an ambient environment of assembly 100) at or near end 101 of assembly 100 and at least one distal or second tube opening 108 that may provide access to passageway 115 (e.g., fluid communication between passageway 115 and an ambient environment of assembly 100) at or near end 109 of assembly 100. Moreover, assembly 100 may also include an expander or expander subassembly 160 that may extend along at least a portion of tube subassembly 110, where expander subassembly 160 may include an external surface 163. As also shown in FIGS. 1-1D, for example, patient 1 may include a passageway wall 13 that may define a passageway 15 that may extend between at least one proximal or first access opening 11 and a distal or second opening 19. Moreover, patient 1 may include a target wall 93 that may define at least a portion of a target space 95, where a proximal or first target opening 91 of wall 93 may be coupled to opening 19 of passageway 15, such that passageway 15 may be fluidly coupled to target space 95. As shown in FIGS. 1-1D, for example, at least a portion of passageway 15 and/or the coupling of opening 19 and opening 91 may have a cross-sectional dimension (e.g., diameter) DO, which may be a minimum dimension of patient 1 through which at least a portion of assembly 100 may pass or otherwise exist during any stage of use within patient 1.

When in an insertion state (see, e.g., FIG. 1), assembly 100 may be inserted into patient 1 to a particular position, and then assembly 100 may be re-configured into an expanded state (see, e.g., FIG. 1A and/or FIG. 1B and/or FIG. 1C) within patient 1 such that assembly 100 may be safely used within patient 1. After use of assembly 100 in its expanded state within patient 1, assembly 100 may be re-configured into a removal state (see, e.g., FIG. 1D) within patient 1 for removal of assembly 100 from patient 1. For example, as shown by FIG. 1, assembly 100 may first be configured in an insertion state or configuration such that assembly 100 may then be at least partially inserted into patient 1. In some embodiments, end 109 of assembly 100 in its insertion state may be inserted into patient 1 in the direction of arrow I through opening 11, through passageway 15, through opening 19, through opening 91, and into target space 95, such that at least one opening 108 of assembly 100 may be within space 95 and/or such that at least one opening 102 of assembly 100 may be accessible to an operator O of assembly 100 (e.g., a physician or nurse or perhaps even patient 1 itself), who may be external to at least passageway 15 of patient 1. Assembly 100 may be of a length LI that may extend between end 101 and end 109 of assembly 100 in its insertion state, and where such a length provided by assembly 100 in its insertion state may vary based on the size of patient 1 and the procedure to be performed. As shown in FIG. 1, when assembly 100 is in its insertion state, no portion of expander 160 may have a cross-sectional dimension (e.g., diameter) greater than dimension DI. In some embodiments, dimension DD of end 109 and dimension DI of expander 160 in the insertion state of assembly 100 may be less than dimension DO of patient 1 such that assembly 100 in its insertion state may be safely inserted into patient 1 without damaging wall 13 and/or wall 93 of patient 1.

After assembly 100 has been inserted into patient 1 while assembly 100 is in its insertion state, assembly 100 may be re-configured into an expanded state within patient 1 such that assembly 100 may thereafter be safely used within patient 1. For example, as shown in each one of FIGS. 1A-1C, once assembly 100 in its insertion state has been inserted into its insertion position of FIG. 1 within patient 1, assembly 100 may be re-configured into an expanded state within patient 1 such that assembly 100 may thereafter be safely used in that expanded state within patient 1. As shown in each one of FIGS. 1A-1C, when assembly 100 is in its expanded state, at least a portion of expander 160 may have a maximum cross-sectional dimension (e.g., diameter) DE that may be at least equal to or greater than dimension DO of patient 1, such that at least a portion of wall 163 of expander 160 may contact or otherwise interact with at least a portion of wall 93 of target 95 and/or with at least a portion of wall 13 of passageway 15 for safely securing expanded assembly 100 at a particular position within patient 1 and/or for safely preventing certain material from traveling between wall 163 of expander 160 and at least a portion of wall 93 of target 95 and/or at least a portion of wall 13 of passageway 15. One or more of dimensions DE, DI, and DR (e.g., as described below) may be widths defined by expander 160, where such a width may be perpendicular to the length of expander 160 (e.g., along the X-axis, which may be perpendicular to the length extending between ends 161 and 169 of expander 160 along the Y-axis). As shown in FIG. 1A, for example, all of expander 160 may be positioned within target space 95 when assembly 100 is re-configured from its insertion state into its expanded state, such that at least a portion of wall 163 of expander 160 may contact or otherwise interact with at least a portion of wall 93 of target 95. Alternatively, as shown in FIG. 1B, for example, all of expander 160 may be positioned within passageway 15 when assembly 100 is re-configured from its insertion state into its expanded state, such that at least a portion of wall 163 of expander 160 may contact or otherwise interact with at least a portion of wall 13 of passageway 15. Alternatively, as shown in FIG. 1C, for example, a first portion of expander 160 may be positioned within passageway 15 and a second portion of expander 160 may be positioned with target space 95 when assembly 100 is re-configured from its insertion state into its expanded state, such that at least a first portion of wall 163 of expander 160 may contact or otherwise interact with at least a portion of wall 13 of passageway 15 and such that at least a second portion of wall 163 of expander 160 may contact or otherwise interact with at least a portion of wall 93 of target 95. As shown in FIGS. 1A-1C, at least a portion of expander 160 may expand at least along the X-axis such that a maximum cross-sectional dimension (e.g., diameter) of expander 160 may expand from dimension DI to dimension DE when assembly 100 is reconfigured from its insertion state to its expanded state. As shown in FIGS. 1A-1C, assembly 100 may be of a length LE that may extend between end 101 and end 109 of assembly 100 in its expanded state, where such a length LE provided by assembly 100 may vary based on the size of patient 1 and may be greater than, less than, or equal to length LI of assembly 100 in its insertion state (e.g., the state of FIG. 1) and/or length LR of assembly 100 in its removal state (e.g., the state of FIG. 1D, described below).

Once assembly 100 has been expanded into its expanded state within patient 1 (e.g., as shown in any one or more of FIGS. 1A-1C), assembly 100 may be safely used within patient 1 in any suitable way, such as in any suitable intubation process. For example, in some embodiments, expanded assembly 100 may be safely used within patient 1 for injecting material (e.g., treatment material, such as nutrients or medicine or oxygen or air) through opening 102, into and through passageway 115, then out of passageway 115 through opening 108, and into target space 95 of patient 1, and/or for removing material (e.g., treatment material, such as waste) from target space 95, through opening 108, into and through passageway 115, then out of passageway 115 through opening 102 away from patient 1. In certain embodiments, target space 95 may be a stomach, opening 91 may be a lower esophageal sphincter, passageway 15 may be an esophagus, pharynx, throat, and/or nasal cavity, and opening 11 may be a nostril or mouth of patient 1, where assembly 100 may be used during a nasogastric intubation process. In other embodiments, target space 95 may be a bladder, opening 91 may be a sphincter, passageway 15 may be a urethra, and opening 11 may be a urinary meatus of patient 1, where assembly 100 may be used during any suitable process that might otherwise use a Foley catheter. It is to be understood that assembly 100 may be used with respect to any suitable portions of any suitable patient 1 for any suitable process, where expander 160 may be expanded such that at least a portion of wall 163 of expander 160 may contact or otherwise interact with at least a portion of wall 93 of target 95 and/or with at least a portion of wall 13 of passageway 15 for safely securing expanded assembly 100 at a particular position within patient 1 (e.g., for preventing opening 108 and/or end 109 of assembly 100 from being inadvertently removed from target space 95 (e.g., in the direction of arrow R) and/or from being inadvertently inserted too far into space 95 (e.g., in the direction of arrow I), such as when assembly 100 may be used as a Foley catheter) and/or for safely preventing certain material from traveling between wall 163 of expander 160 and at least a portion of wall 93 of target 95 and/or between wall 163 of expander 160 and at least a portion of wall 13 of passageway 15 (e.g., for preventing contents of a stomach target 95 from escaping target 95 through passageway 15 about the exterior of wall 163 of expander 160 (i.e., not through assembly 100), such as towards a trachea or other portion of patient 1 between expander 160 and end 11 of passageway 15 that may cause infections and/or inflammation (e.g., in the direction of arrow R), such as when assembly 100 may be used as a nasogastric tube). Specifically, reflux of contents from the stomach back into the esophagus has been a persistent problem, especially in the presence of nasogastric tubes. Contents often attempt to travel back up from the stomach around the tube, thereby causing reflux esophagitis, aspiration pneumonitis, and/or pneumonias.

After assembly 100 has been used in its expanded state within patient 1, assembly 100 may be re-configured into a removal state such that assembly 100 may thereafter be safely removed from within patient 1 (e.g., in the direction of arrow R). For example, as shown in FIG. 1D, once assembly 100 has been used in its expanded state of any of FIGS. 1A-1C within patient 1, assembly 100 may be re-configured into a removal state within patient 1 such that assembly 100 may thereafter be safely removed in its removal state from within patient 1. For example, as shown in FIG. 1D, when assembly 100 is in its removal state, no portion of expander 160 may have a cross-sectional dimension (e.g., diameter) greater than dimension DR, where such a dimension DR provided by assembly 100 may vary based on the size of patient 1 and may be greater than, less than, or equal to dimension DI of the insertion state. In some embodiments, dimension DD of end 109 and dimension DR of expander 160 in the removal state of assembly 100 may be less than dimension DO of patient 1 such that assembly 100 in its removal state may be safely removed from patient 1 without damaging wall 13 and/or wall 93 of patient 1. In some embodiments, as shown in FIG. 1D, at least a portion of expander 160 may contract at least along the X-axis such that a maximum cross-sectional dimension (e.g., diameter) of expander 160 may contract from dimension DE to dimension DR when assembly 100 is reconfigured from its expanded state to its removal state. As shown in FIG. 1D, assembly 100 may be of a length LR that may extend between end 101 and end 109 of assembly 100 in its removal state, where such a length LR provided by assembly 100 may vary based on the size of patient 1 and may be greater than, less than, or equal to length LI of assembly 100 in its insertion state and/or length LE of assembly 100 in its expanded state. It is to be noted that, while "proximal" or "proximate" may be used herein to refer to a general direction or end of assembly 100 that may be closest to operator O of assembly 100 during use (e.g., external to patient 1), and while "distal" or "distant" may be used herein to refer to a general direction or end of assembly 100 that may be farthest from operator O of assembly 100 during use (e.g., within target 95), such directional and orientational terms may be used herein only for convenience, and that no fixed or absolute directional or orientational limitations are intended by the use of these words.

In some embodiments, expander subassembly 160 may include a balloon (e.g., a high volume, low pressure balloon) or any other suitable expander mechanism or component that may be inflatable by air or any other suitable fluid (e.g., gas or liquid or any other suitable substance that may be able to flow into and/or out of the expander mechanism) for enabling the expansion of at least a portion of expander subassembly 160 (e.g., from dimension DI to dimension DE), which may allow at least a portion of expander subassembly 160 to contact a wall of patient 1 for securing expanded assembly 100 at a particular position within patient 1 and/or for preventing certain material from traveling between expander subassembly 160 and a wall of patient 1.

Figure 2:
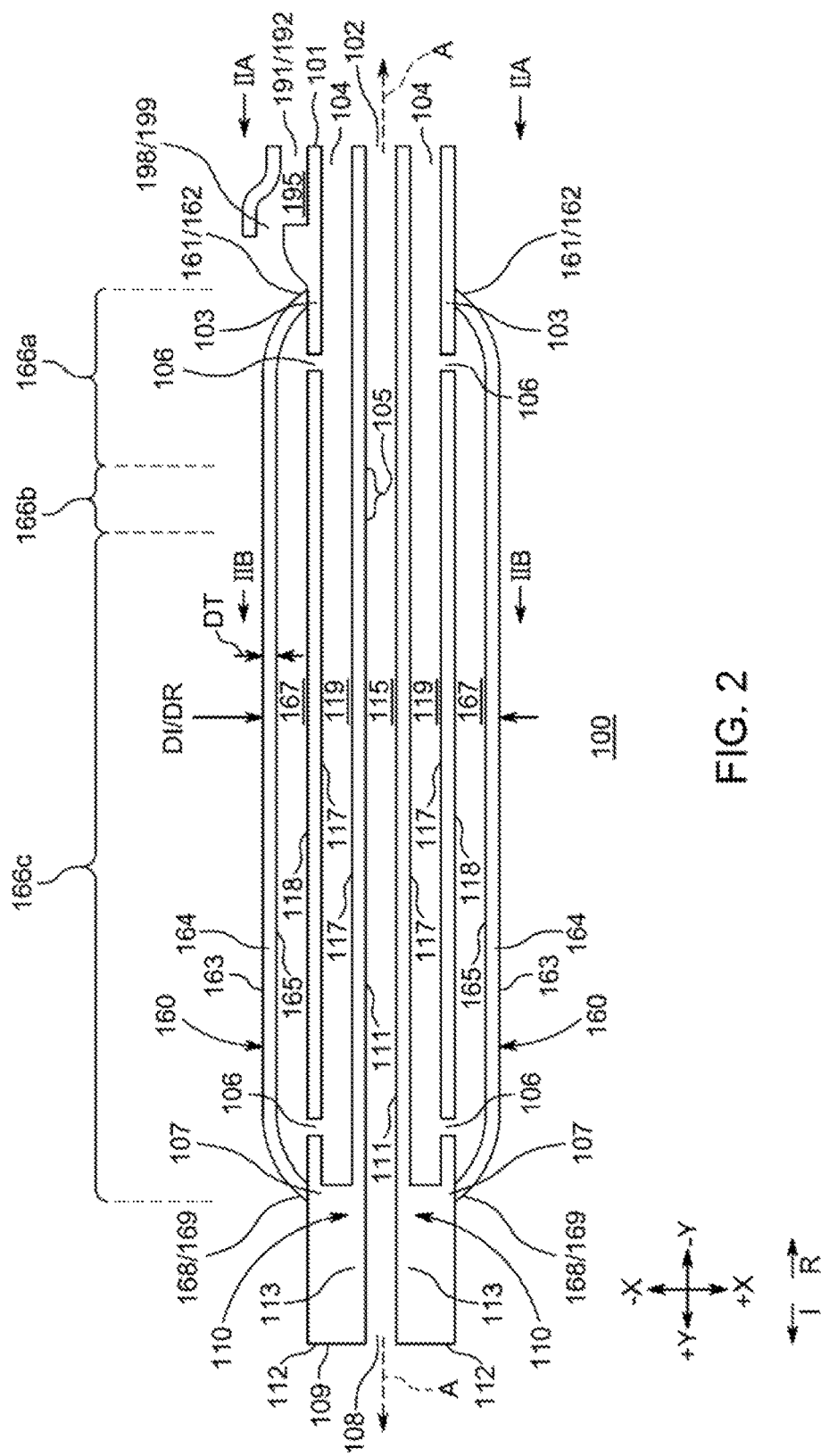
FIG. 2 is a side elevational view of the intubation assembly of FIGS. 1-1D in an insertion state.
Figure 2B:
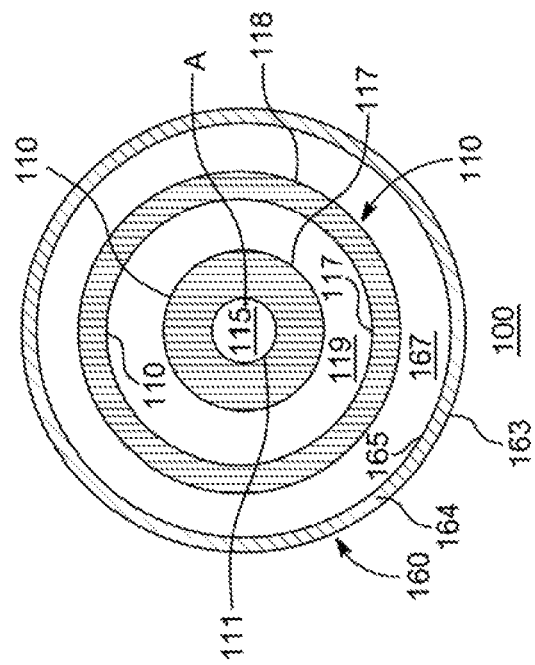
FIG. 2B is a cross-sectional view of the intubation assembly of FIGS. 2 and 2A taken from line IIB-IIB of FIG. 2.
Figure 2A:
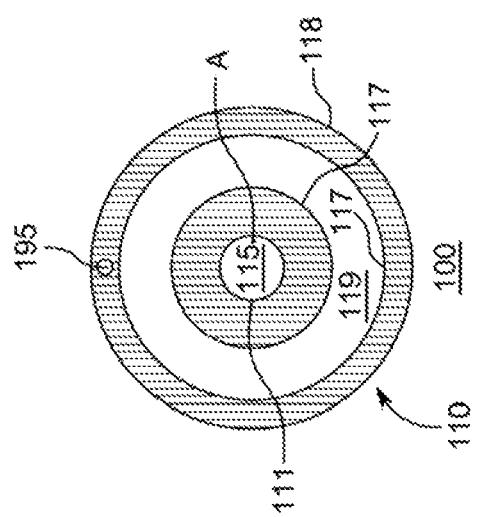
FIG. 2A is a cross-sectional view of the intubation assembly of FIG. 2 taken from line IIA-IIA of FIG. 2.
Figure 3:
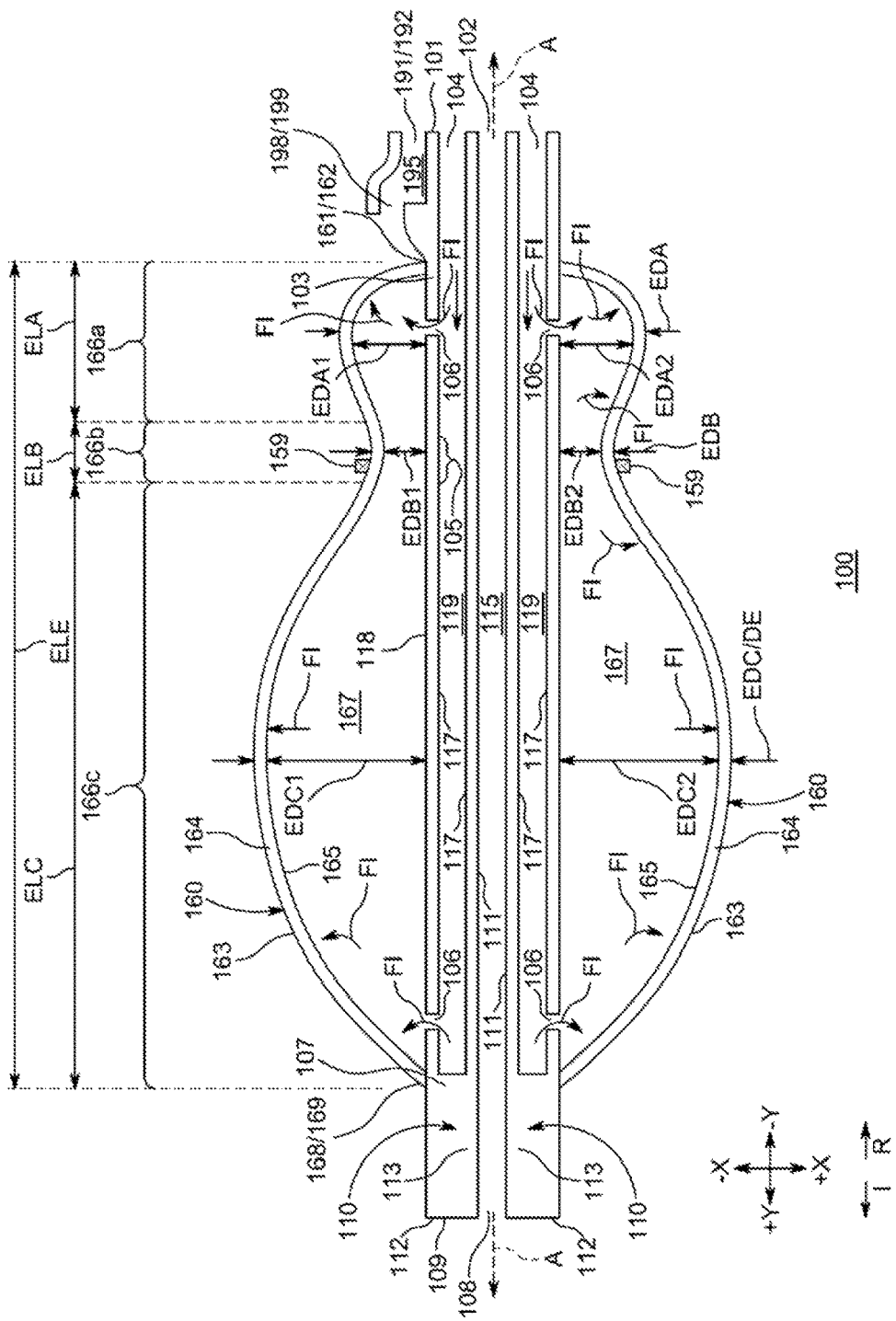
FIG. 3 is a cross-sectional view of the intubation assembly of FIGS. 2-2B in an equilibrium geometry of an expanded state.

As shown in FIGS. 2-7, for example, assembly 100 may include tube subassembly 110 and expander subassembly 160 with such an expander component 164. Tube subassembly 110 may provide a body structure 112 that may include tube wall(s) 113 that may provide one or more surfaces 111 that may define at least first passageway 115 for extending between at least first tube opening 102 that may provide access to passageway 115 at or near end 101 of assembly 100 and at least one distal or second tube opening 108 that may provide access to passageway 115 at or near end 109 of assembly 100, such that, when assembly 100 is appropriately positioned at least partially within patient 1, material may be injected through opening 102, into and through passageway 115, then out of passageway 115 through opening 108, and into target space 95 of patient 1, and/or such that material may be removed from target space 95, through opening 108, into and through passageway 115, then out of passageway 115 through opening 102 away from patient 1. For example, as shown in FIGS. 2-3, passageway 115 may be a single passageway extending along a longitudinal axis of tube subassembly 110 (e.g., axis A that may extend along a Y-axis), although, in other embodiments, passageway 115 may be provided by two or more passageways, at least one of which may at least partially not extend along a longitudinal axis of tube subassembly 110. In some embodiments, although not shown, opening 102 may not be provided at end 101 of assembly 100 but may instead be provided along and/or through a side surface of tube walks) 113 proximal to end 101, and/or opening 108 may not be provided at end 109 of assembly 100 but may instead be provided along and/or through a side surface of tube wall(s) 113 proximal to end 109. Tube wall(s) 113 of subassembly 110 may also provide one or more exterior surfaces 118 of tube subassembly 110 along at least a portion of the length of tube subassembly 110 between ends 101 and 109.

Expander subassembly 160 may include any suitable expander component 164 that may provide exterior surface 163 and interior surface 165 extending between first or proximal expander end 161 and second or distal expander end 169. Expander component 164 may include at least one proximal or first expander opening 162 at or near end 161 and at least one distal or second expander opening 168 at or near end 169. As shown, expander subassembly 160 may be coupled to tube subassembly 110 such that an expander passageway 167 may be provided between interior surface 165 of expander component 164 and along and about exterior surface 118 of tube assembly 110 between ends 161 and 169 of expander component 164. For example, first expander opening 162 may be coupled to and about exterior surface 118 of tube assembly 110 at a first position 103 along the length of tube subassembly 110 using any suitable coupling technique (e.g., adhesive, molding (e.g., blow molding), crimping, etc.) and second expander opening 168 may be coupled to and about exterior surface 118 of tube assembly 110 at a second position 107 along the length of tube subassembly 110 using any suitable coupling technique (e.g., adhesive, molding (e.g., blow molding), crimping, etc.) such that expander passageway 167 may be provided between interior surface 165 of expander component 164 and exterior surface 118 of tube assembly 110 at least partially along the length of expander component 164 between ends 161 and 169. Expander component 164 may be a balloon (e.g., a high volume, low pressure balloon) or any other suitable expander mechanism or component that may be made of any suitable material (e.g., polyurethane, silicone, rubber, polyethylene terephthalate ("PET"), nylon, and/or the like) and/or that may be at least semi-compliant and that may define a space that may be inflatable by air or any other suitable fluid (e.g., gas or liquid or any other suitable substance that may be able to flow into and/or out of the expander mechanism), such that the space may change shape when pressure therein may change.

Tube wall(s) 113 of subassembly 110 may also provide one or more surfaces 117 of tube subassembly 110 that may define at least one inflation passageway 119 for extending between at least one other proximal or third tube or inflation opening 104 that may provide access to passageway 119 (e.g., fluid communication between passageway 119 and an ambient environment of body structure 112 of subassembly 110) at or near end 101 of assembly 100 and at least one distal or fourth tube or inflation opening 106 that may provide access to passageway 119 (e.g., fluid communication between passageway 119 and an ambient environment of body structure 112 of subassembly 110) at a position along the length of assembly 100 distal of opening 104 (e.g., between positions 103 and 107 along the length of subassembly 110), where opening 106 may be operative to fluidly couple passageway 119 of tube subassembly 110 to expander passageway 167 of expander subassembly 160 (e.g., between positions 103 and 107 along the length of subassembly 110). For example, as shown in FIGS. 2-3, passageway 119 may be a single passageway extending concentrically about a longitudinal axis of tube subassembly 110 (e.g., axis A) and/or concentrically about passageway 115, although, in other embodiments, passageway 119 may be provided by one or two or more distinct passageways, each of which may extend along and adjacent passageway 115 but not entirely about passageway 115. In some embodiments, although not shown, at least one opening 104 may not be provided at end 101 of assembly 100 but may instead be provided along and/or through a side surface of tube wall(s) 113 proximal to end 101. As shown in FIGS. 2-3, two or more tube openings 106 may be provided through tube wall(s) 113 of tube subassembly 110 (e.g., between surfaces 117 and 118), each of which may be operative to fluidly couple passageway 119 of tube subassembly 110 to expander passageway 167 of expander subassembly 160 (e.g., a first tube opening 106 may be positioned proximate end 161 of expander subassembly 160 while a second tube opening 106 may be positioned proximate end 169 of expander subassembly 160), while, in other embodiments, only a single tube opening 106 may be provided for coupling passageways 119 and 167.

Figure 4:
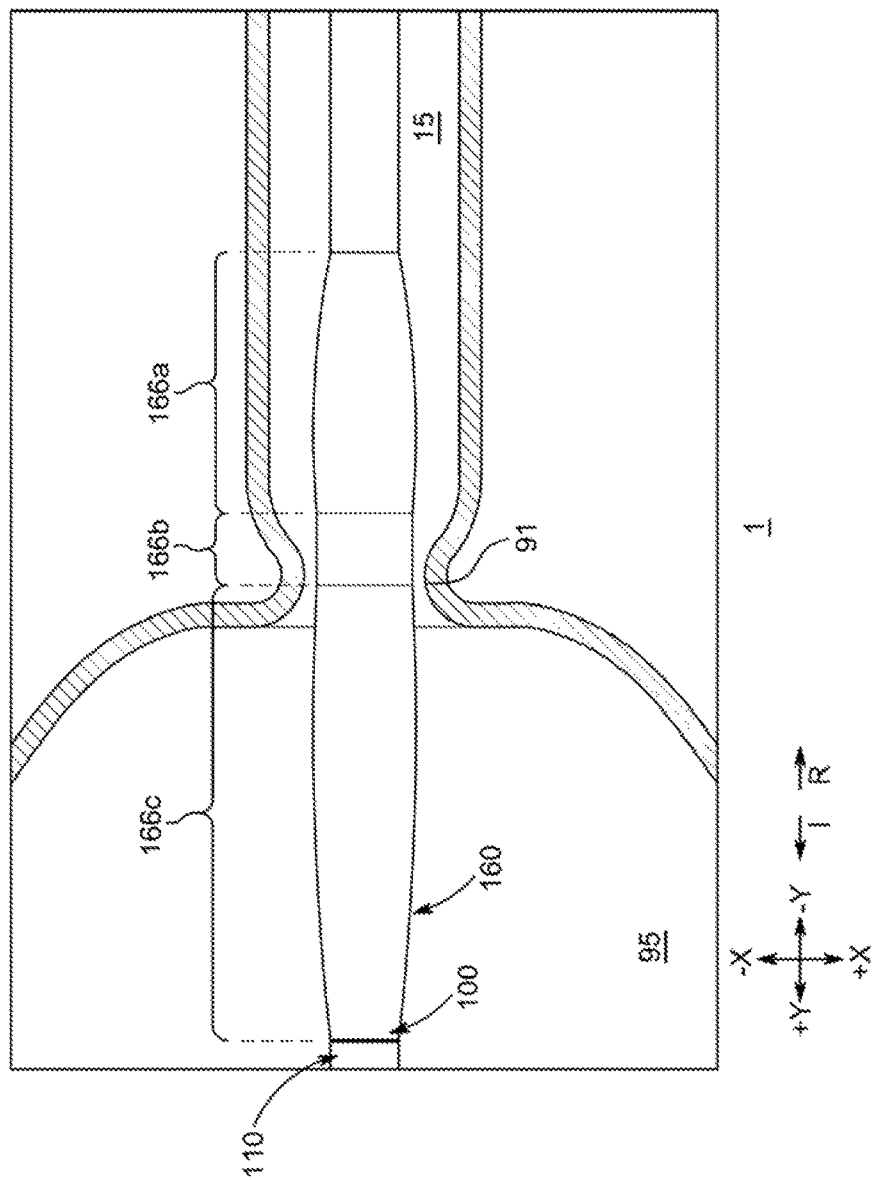
FIG. 4 is a side elevational view of the intubation assembly of FIGS. 2-3 in the insertion state within a patient.
Figure 5:
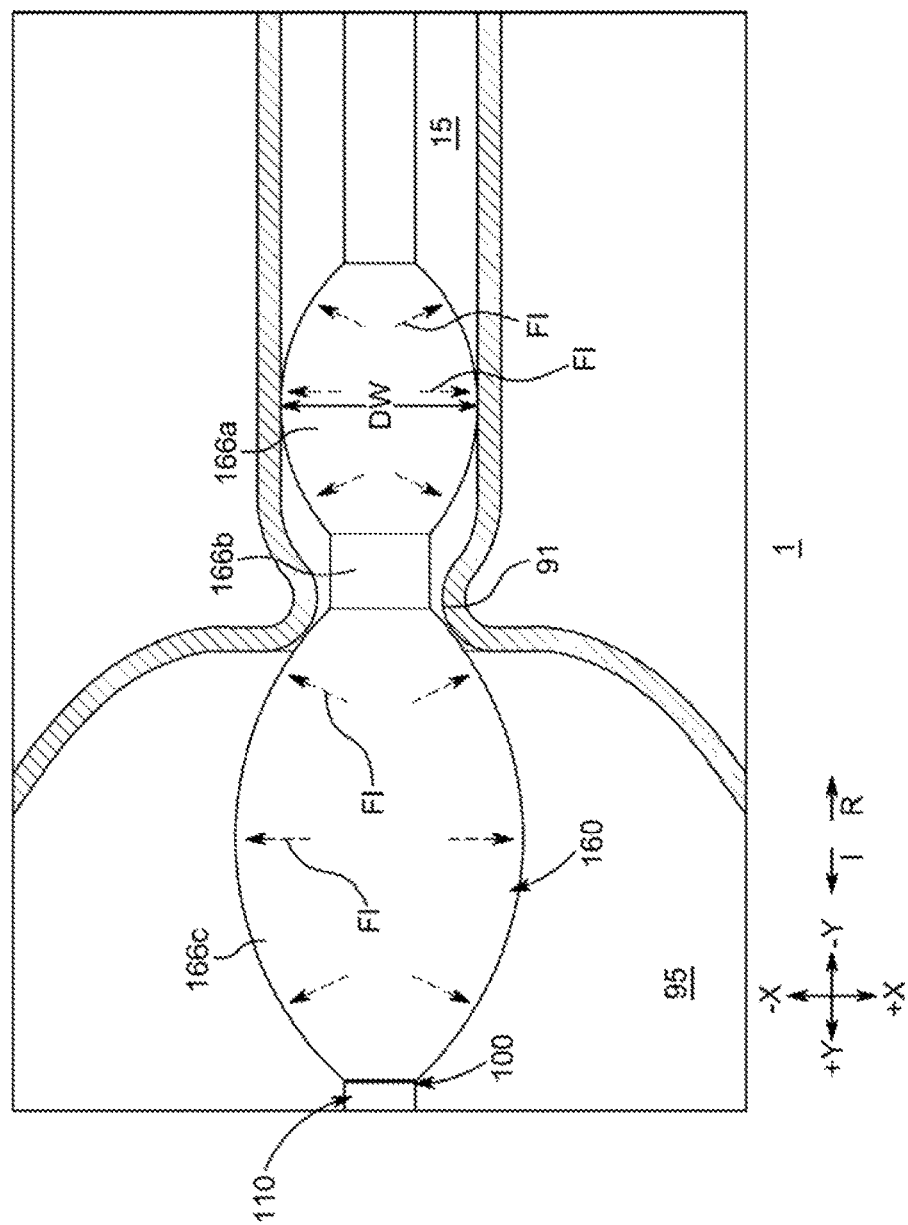
FIG. 5 is a side elevational view of the intubation assembly of FIGS. 2-4 in the equilibrium geometry of the expanded state within a patient.
Figure 6:
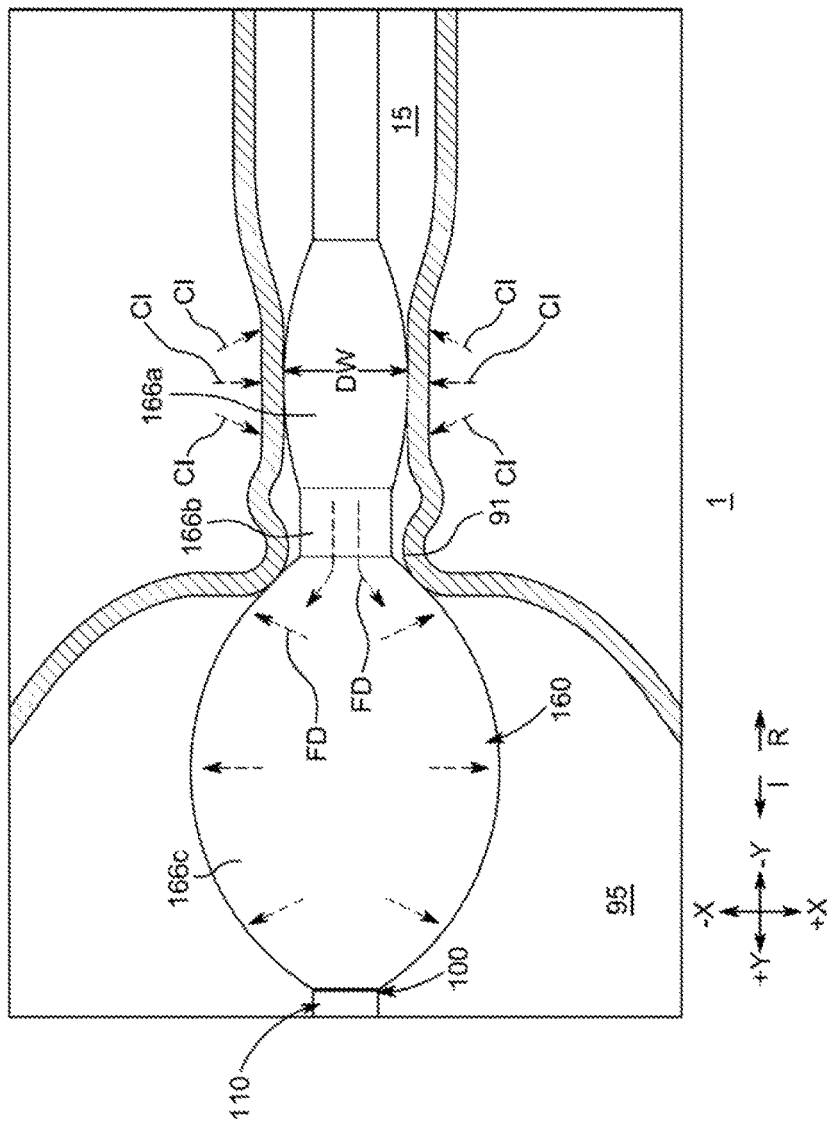
FIG. 6 is a side elevational view of the intubation assembly of FIGS. 2-5 in a deformed geometry of the expanded state within a patient.
Figure 7:
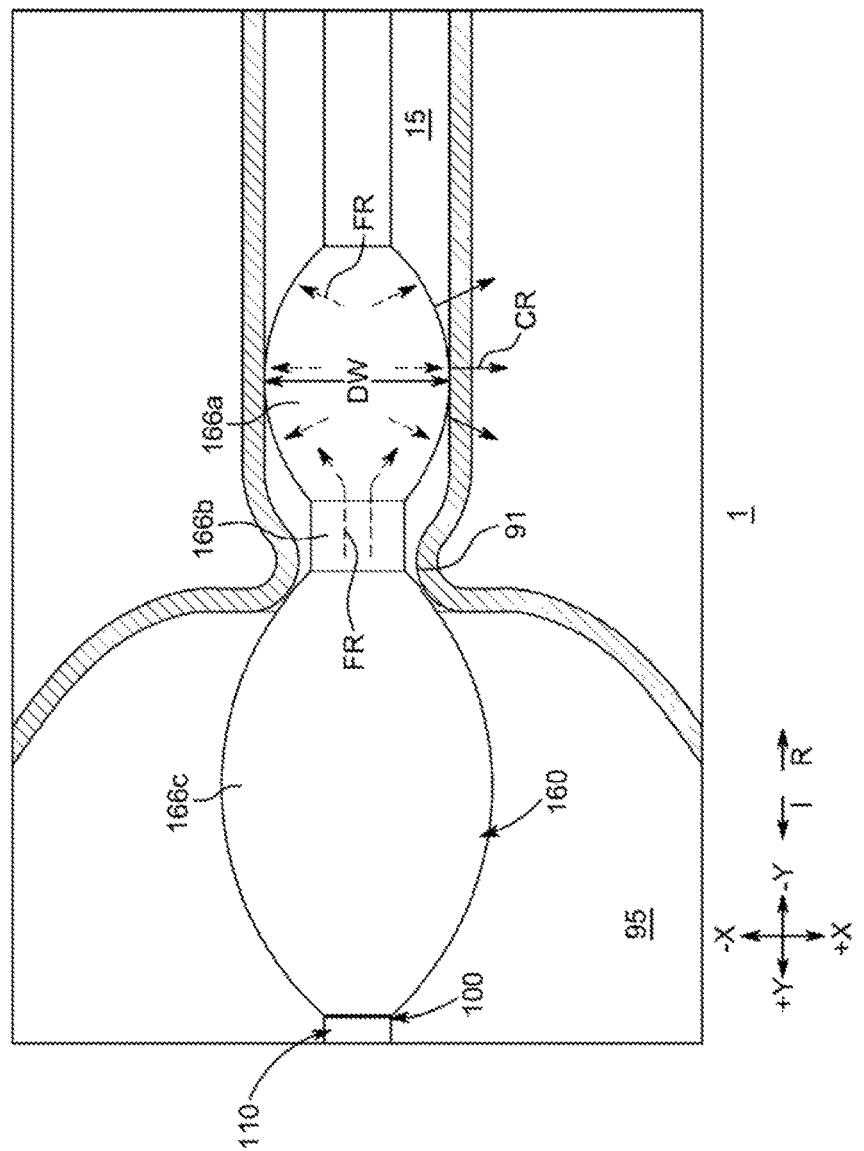
FIG. 7 is a side elevational view of the intubation assembly of FIGS. 2-6 in the equilibrium geometry of the expanded state within a patient.

Any suitable fluid (e.g., air or a liquid or a combination thereof) may be injected (e.g., by operator O using any suitable fluid delivery system (not shown)) through at least one opening 104, into and through passageway 119, then out of passageway 119 through at least one tube opening 106, and then into expander passageway 167 for at least partially inflating expander component 164 about tube subassembly 110 for reconfiguring expander subassembly 160 from a natural or relaxed or un-inflated state (e.g., when no external forces of assembly 100 are being applied to expander component 164 (e.g., as shown in FIGS. 2 and 4)) into an unnatural or tensioned or at least partially inflated state (e.g., when the injected fluid within expander passageway 167 applies forces to expander component 164 (e.g., as shown in FIGS. 3 and 5-7)), which may reconfigure assembly 100 from an insertion state (e.g., as shown in FIGS. 1 and 2 and 4) into an expanded state (e.g., as shown in FIGS. 1A and 3 and 5-7). Any suitable volume of such injected fluid may be retained within the combined space defined by fluidly coupled passageways 119 and 167, for example, by capping opening 104. Passageway 119 may be of a fixed volume when body structure 112 may be any suitable rigidity to prevent a collapse of the shape of passageway 119, while the volume of passageway 167 may change based on the amount of fluid retained within the combined space of fluidly coupled passageways 119 and 167. Additionally or alternatively, any suitable fluid (e.g., air or liquid) may be removed (e.g., by operator O using any suitable fluid removal system (not shown)) from expander passageway 167 through at least one tube opening 106, into and through passageway 119, then out of passageway 119 through at least one opening 104 for at least partially deflating expander component 164 about tube subassembly 110 for reconfiguring expander subassembly 160 from an unnatural or tensioned or at least partially inflated state (e.g., when the fluid within expander passageway 167 to be removed applies forces to expander component 164 (e.g., as shown in FIGS. 3 and 5-7)) into a natural or relaxed or un-inflated state (e.g., when no fluid within expander passageway 167 applies force to expander component 164 (e.g., as shown in FIGS. 2 and 4)), which may reconfigure assembly 100 from an expanded state (e.g., as shown in FIGS. 1A and 3 and 5-7) into a removal state (e.g., as shown in FIGS. 1D and 2 and 4). Expander subassembly 160 may be coupled to tube subassembly 110 and configured such that expander subassembly 160 (e.g., expander component 164) may be expanded to an equilibrium geometry of a particular unnatural or tensioned or at least partially inflated state of FIGS. 3 and 5 and 7 when a particular amount (e.g., volume (e.g., a volume of 30 cubic centimeters or 50 cubic centimeters or any other suitable amount)) of fluid is injected into assembly 100 through opening 104 and retained within assembly 100 (e.g., within passageways 119 and 167) but when no external force may be applied to expander subassembly 160 (e.g., by patient 1 (e.g., by constricting walls 13 of patient passageway 15)). Such a particular inflated state of expander subassembly 160 may define a structure of any suitable particular equilibrium geometry. For example, as shown in FIGS. 3 and 5 and 7, the particular equilibrium geometry of a particular inflated state of expander subassembly 160 may include a proximal or first expander component section 166a, an intermediate or second expander component section 166b, and a distal or third expander component section 166c, where first expander component section 166a may extend between position 103 and a section 105 along a length ELA of tube subassembly 110 with a maximum cross-sectional dimension (e.g., diameter) EDA, where second expander component section 166b may extend along section 105 along a length ELB of tube subassembly 110 with a maximum cross-sectional dimension (e.g., diameter) EDB, and where third expander component section 166c may extend between section 105 and position 107 along a length ELC of tube subassembly 110 with a maximum cross-sectional dimension (e.g., diameter) EDC. Expander subassembly 160 may be manufactured and/or coupled to tube subassembly 110 and/or inflated in any suitable manner(s) such that the equilibrium geometry of a particular inflated state of expander subassembly 160 may be operative to retain the portion of patient 1 at opening 91 of target space 95 between first expander component section 166a and third expander component section 166c (e.g., along second expander component section 166b) when assembly 100 is in its expanded state and appropriately positioned within patient 1 (see, e.g., FIG. 5). In some embodiments, ELA may be about 3-7 centimeters and/or ELC may be about 2-4 centimeters and/or ELB may be about 0.5-5 centimeters. Expander component section 166a may include a tooth-shape and/or a cylindrical shape or disc shaped or any other suitable shape along length ELA (e.g., when expanded), and/or expander component section 166c may be spherical or disc shaped or any other suitable shape along length ELC (e.g., when expanded) to minimize its volume, where EDC may be about 5-7 centimeters while ELC may be about 2-4 centimeters in the equilibrium expanded state of expander assembly 160. In some embodiments, as shown, the geometry of a particular inflated state of one, some, or each expander component section of expander subassembly 160 may be symmetrical or asymmetrical about longitudinal axis A of tube subassembly 110. For example, a maximum cross-sectional dimension (e.g., diameter) EDA1 of first expander component section 166a between a first (e.g., top) side of tube subassembly 110 and expander component 164 may be the same as or different than a maximum cross-sectional dimension (e.g., diameter) EDA2 of first expander component section 166a between a second (e.g., bottom) side of tube subassembly 110 and expander component 164 (e.g., opposite sides with respect to longitudinal axis A), and/or a maximum cross-sectional dimension (e.g., diameter) EDB1 of second expander component section 166b between a first (e.g., top) side of tube subassembly 110 and expander component 164 may be the same as or different than a maximum cross-sectional dimension (e.g., diameter) EDB2 of second expander component section 166b between a second (e.g., bottom) side of tube subassembly 110 and expander component 164 (e.g., opposite sides with respect to longitudinal axis A), and/or a maximum cross-sectional dimension (e.g., diameter) EDC1 of third expander component section 166c between a first (e.g., top) side of tube subassembly 110 and expander component 164 may be the same as or different than a maximum cross-sectional dimension (e.g., diameter) EDC2 of third expander component section 166c between a second (e.g., bottom) side of tube subassembly 110 and expander component 164 (e.g., opposite sides with respect to longitudinal axis A). In some embodiments, second expander component section 166b may be prevented from expanding beyond a particular cross-sectional dimension of its equilibrium geometry due to the structural composition of expander component 164 (e.g., despite at least a portion of first expander component section 166a and/or at least a portion of third expander component section 166c being able to expand beyond a particular cross-sectional dimension of its equilibrium geometry (see, e.g., an increase in a dimension of third expander component section 166c between its equilibrium geometry of FIG. 5 and a varied geometry of FIG. 6)). Alternatively, any suitable mechanism 159, such as a rigid band of material, may be positioned about expander component 164 along at least a portion of second expander component section 166b to prevent second expander component section 166b from expanding beyond maximum cross-sectional dimension (e.g., diameter) EDB of the equilibrium geometry of FIGS. 3 and 5 while still allowing a portion of expander passageway 167 to extend through second expander component section 166b between expander component 164 and surface 118 of tube subassembly 110, where EDB may be about 0.5-1.5 centimeters in the equilibrium expanded state of expander assembly 160. First expander component section 166a may have any suitable pressure (e.g., no greater than 40 mmHg for a particular size patient) when in the equilibrium expanded state of expander assembly 160, such as a pressure operative to retain assembly 160 in a desired functional position within patient 1 while also enabling walls 13 of passageway 15 to naturally contract and expand (e.g., to enable patient 1 to safely breath). Therefore, first expander component section 166a and third expander component section 166c may define distinct portions of expander passageway 167, even when fluidly coupled via a portion of expander passageway 167 defined by second expander component section 166b.

When assembly 100 is in an insertion state (see, e.g., FIGS. 1, 2, and 4, where expander subassembly 160 may be in a natural or relaxed or un-inflated state such that maximum cross-sectional dimension (e.g., diameter) DI of expander subassembly 160 (e.g., cross-sectional dimension (e.g., diameter) of at least third expander component section 166c) may be less than cross-sectional dimension (e.g., diameter) DO of opening 91 and/or of passageway 15 of patient 1), assembly 100 may be inserted (e.g., in the direction of arrow I) into patient 1 to a particular position (e.g., a position at which at least a portion of third expander component section 166c may be positioned within target space 95 of patient 1 and a position at which at least a portion of first expander component section 166a may be positioned within passageway 15 of patient 1 and/or a position at which at least a portion of second expander component section 166b may be positioned within or proximate opening 91 of patient 1), as shown in FIG. 4. Then, assembly 100 may be re-configured into an expanded state (see, e.g., FIGS. 1A, 3, and 5, where expander subassembly 160 may be in a particular unnatural or tensioned or at least partially inflated state such that maximum cross-sectional dimension (e.g., diameter) DE of expander subassembly 160 (e.g., at least dimension EDC of third expander component section 166c) may be greater than cross-sectional dimension (e.g., diameter) DO of opening 91 of patient 1) within patient 1, as shown in FIG. 5 (e.g., when a particular amount (e.g., volume) of fluid is injected (e.g., by operator O in the direction of arrows FI of FIGS. 3 and 5) into assembly 100 through opening 104 and retained within assembly 100 (e.g., within passageways 119 and 167) but when no external force may be applied to expander subassembly 160 (e.g., by patient 1 (e.g., by constricting walls of patient passageway 15 on first expander component section 166a)). In such a particular unnatural or tensioned or at least partially inflated state of FIGS. 1A, 3, and 5, the volume of fluid within expander subassembly 160 may be set such that the pressure of first expander component section 166a may be less than 40 mmHg (e.g., based on the volume of fluid injected into subassembly 160 and the difference in volumes between first expander component section 166a and third expander component section 166c) or any other suitable volume that may be operative to at least partially secure assembly 100 in the functional position of FIGS. 1A, 3, and 5 within patient 1 (e.g., such that dimension EDA of first expander component section 166a may be larger than dimension DO of opening 19/91 to resist insertion of first expander component section 166a into target space 95 and/or such that dimension EDA of first expander component section 166a may contact or otherwise interact with at least a portion of wall 13 of passageway 15 for safely securing expanded assembly 100 at a particular position within patient 1 and/or for safely preventing certain material from traveling between wall 163 of first expander component section 166a and at least a portion of wall 13 of passageway 15) but that may also be operative not to prevent or resist contraction of passageway 15 (e.g., contraction of cross-sectional dimension DW of passageway 15 of FIGS. 5-7 (e.g., due to patient 1 swallowing)). Therefore, the particular unnatural or tensioned or at least partially inflated state of FIGS. 1A, 3, and 5 of first expander component section 166a may be configured (e.g., based on the geometry of first expander component section 166a and the volume of fluid within first expander component section 166a in such a state (e.g., within the portion of passageway 167 defined by first expander component section 166a in such a state)) to provide a pressure that may achieve these goals of assembly positioning and assembly functionality and patient safety (e.g., a pressure of no more than 40 mmHG, such that pressure of 40 mmHG or greater by walls of the patient may be operative to deform first expander component section 166a). The bigger the ratio of the volume of first expander component section 166a to the volume of third expander component section 166c is, the more pressure there may be for first expander component section 166a (e.g., if the volume of third expander component section 166c is much larger than the volume of first expander component section 166a, the pressure of first expander component section 166a may be lower). As shown in FIGS. 3 and 5, when assembly 100 is in its expanded state, at least a portion of expander subassembly 160 may have a cross-sectional dimension (e.g., at least a portion of third expander component section 166c may have a cross-sectional dimension) that may be at least equal to or greater than dimension DO of opening 19/91 of patient 1, such that at least a portion of surface 163 of expander component 164 of expander subassembly 160 may contact or otherwise interact with at least a portion of wall 93 of target 95 for safely securing at least a portion of expanded assembly 100 at a particular position within patient 1 (e.g., for securing at least a portion of third expander component section 166c within target 95 and/or for resisting and/or preventing that portion from passing in the direction of arrow R through opening 91 and into passageway 15) and/or for safely preventing certain material from traveling between surface 163 of expander component 164 and at least a portion of wall 93 of target 95 and/or at least a portion of wall 13 of passageway 15 (e.g., such that movement of any material between target space 95 and passageway 15 about the exterior of assembly 100 in its expanded state may be limited or prevented). Additionally or alternatively, as shown in FIGS. 3 and 5, when assembly 100 is in its expanded state, at least a portion of expander subassembly 160 may have a cross-sectional dimension (e.g., at least a portion of first expander component section 166a may have a cross-sectional dimension) that may be at least equal to or greater than dimension DO of opening 19/91 of patient 1, such that at least a portion of surface 163 of expander component 164 of expander subassembly 160 may contact or otherwise interact with at least a portion of wall 13 of passageway 15 for safely securing at least a portion of expanded assembly 100 at a particular position within patient 1 (e.g., for securing at least a portion of first expander component section 166a within passageway 95 and/or for resisting and/or preventing that portion from passing in the direction of arrow I through opening 19 and into target space 95) and/or for safely preventing certain material from traveling between surface 163 of expander component 164 and at least a portion of wall 93 of target 95 and/or at least a portion of wall 13 of passageway 15 (e.g., such that movement of any material between target space 95 and passageway 15 about the exterior of assembly 100 in its expanded state may be limited or prevented). In some embodiments, the maximum cross-sectional dimension (e.g., diameter) EDC of third expander component section 166c may be larger than maximum cross-sectional dimension (e.g., diameter) EDA of first expander component section 166a in a particular inflated state (e.g., the state of FIGS. 3 and 5) and/or the maximum cross-sectional dimension of each one of third expander component section 166c and first component section 166a may be larger than the maximum cross-sectional dimension EDB of second expander component section 166b (e.g., to match the sizes of target space 95, opening 19/91, and passageway 15 within which respective expander components 166c, 166b, and 166a may be positioned in the functional position of expanded assembly 100 of FIG. 5). When in the functional position of FIG. 5, material may be passed through expanded subassembly 100 (e.g., through passageway 115 of tube subassembly 110) between target space 95 and passageway 15, either in the direction of arrow I or in the direction of arrow R.

Although the amount (e.g., volume) of fluid that may be injected into and then held within expander passageway 167 of assembly 100 when assembly 100 is in the particular expanded state of FIGS. 3 and 5 may be fixed or predetermined, a dimension of at least a portion of patient 1 may vary during use of assembly 100 in that state. For example, cross-sectional dimension DW of passageway 15 may expand and/or contract while assembly 100 is positioned within patient 1, such as due to patient 1 swallowing and/or due to involuntary contractions of wall 13. Assembly 100 may be configured to alter its geometry in conjunction with such variation of patient 1 so that assembly 100 may maintain its ability to maintain the position of assembly 100 within patient 1 (e.g., to maintain at least a portion of expander component 160 within target space 95 (e.g., at least a portion of third expander component section 166c distal to opening 19/91) and to maintain at least a portion of expander component 160 within passageway 15 (e.g., at least a portion of first expander component section 166a proximal to opening 19/91)). For example, as shown between FIGS. 5 and 6, expander subassembly 160 may be configured such that, in a particular inflated state (e.g., of FIGS. 3 and 5-7 (e.g., with a fixed particular amount of fluid within passageway 167)), when walls of patient 1 may contract or squeeze against expander subassembly 160 or otherwise reduce the cross-sectional dimension DW or any other suitable cross-sectional dimension of passageway 15 (e.g., in the direction of arrows CI of FIG. 6), first expander component section 166a may be operative to at least partially or fully deflate by passing fluid from within a portion of passageway 167 of first expander component section 166a to within a portion of passageway 167 of third expander component section 166c (e.g., in the direction of arrows FD of FIG. 6 (e.g., via a portion of passageway 167 of second expander component section 166b and/or via passageway 119 and two or more different openings 106)), thereby further inflating third expander component section 166c (e.g., increasing its inflated volume, which may increase its cross-sectional dimension EDC and/or its length ELC). Therefore, while expander subassembly 160 may be configured to have an equilibrium geometry of FIGS. 3 and 5 when a particular amount of fluid is held within expander passageway 167 for a particular expanded state of assembly 100 (e.g., when no external forces are applied to assembly 100 (e.g., by patient 1)), expander subassembly 160 may also be configured to adjust its geometry (e.g., from the equilibrium geometry of FIG. 5 to an adjusted geometry of FIG. 6) when the amount of fluid held within expander passageway 167 remains the same but when an external force is applied to assembly 100 (e.g., by contraction forces in the direction of arrows CI by patient 1) as the external force may deform expander 160 so as to force fluid from one portion of passageway 167 to another portion of passageway 167 (e.g., by forcing fluid to pass from within a portion of passageway 167 of first expander component section 166a to within a portion of passageway 167 of third expander component section 166c (e.g., in the direction of arrows FD of FIG. 6)). Such an adjustment of the geometry of a particular expanded state of assembly 100 between that of FIG. 5 and that of FIG. 6 may maintain a relationship between assembly 100 and patient 1 for maintaining assembly 100 at the functional position within patient 1 (e.g., maintain a larger cross-sectional dimension of third expander component section 166c within target space 95 than that of opening 19/91 to prevent end 109 of assembly 100 from being inadvertently removed from target space 95 and/or maintain a larger cross-sectional dimension of first expander component section 166a within passageway 15 than that of opening 19/91 to prevent end 109 of assembly 100 from being inadvertently inserted further into target space 95 and potentially harming walls 93). Such compressibility of first expander component section 166a may be operative to avoid damage of wall 13 from high pressures (e.g., if wall 13 were to contract and pressure in first expander component section 166a were to rise without compressing (e.g., without fluid being able to leave first expander component section 166a), such a non-compressible first expander component section 166a might explode (e.g., pop) or compress vessels in wall 13, thereby reducing blood supply). Therefore, in some embodiments, a particular equilibrium geometry of a particular inflated state of expander subassembly 160 (e.g., of FIG. 5) may be configured such that some or even all (e.g., at least 25%, at least 50%, at least 75%, or 100%) of the volume of fluid within first expander component section 166a in that equilibrium geometry (e.g., within the portion of passageway 167 defined by first expander component section 166a in that equilibrium geometry) may be transferred to and held within third expander component section 166c (e.g., within the portion of passageway 167 defined by third expander component section 166c) when in a deformed geometry of that particular inflated state (e.g., of FIG. 6) without popping or otherwise rupturing third expander component section 166c or any other portion of expander subassembly 160 (e.g., the volume of fluid within third expander component section 166c in the equilibrium geometry (e.g., within the portion of passageway 167 defined by third expander component section 166c in the equilibrium geometry) combined with some, most, or all of the volume of fluid within first expander component section 166a in the equilibrium geometry (e.g., within the portion of passageway 167 defined by first expander component section 166a in the equilibrium geometry) may together be held within third expander component section 166c (e.g., within the portion of passageway 167 defined by third expander component section 166c) in the deformed geometry without damaging expander subassembly 160). Therefore, third expander component section 166c may not be frilly expanded in its equilibrium geometry but may instead be configured to expand further (e.g., to be filled with more fluid to expand to a greater deformed geometry), while first expander component section 166a may or may not be fully expanded in its equilibrium geometry (e.g., first expander component section 166a may not be able to take on much more fluid than the amount within first expander component section 166a in its equilibrium geometry (e.g., within the portion of passageway 167 defined by first expander component section 166a in its equilibrium geometry)). The material of expander component 164 (e.g., as semi-compliant or compliant) may be operative to enable expansion of third expander component section 166c by accommodating more volume (e.g., to prevent rising pressure in first expander component section 166a (e.g., due to compression of first expander component section 166a that may lead to expulsion of air from first expander component section 166a into third expander component section 166c)). First expander component section 166a may be configured to expand to its inflated state with no more than a particular maximum pressure (e.g., a pressure of no more than 40 mmHG, such that pressure of 40 mmHG or greater by walls of the patient (e.g., during contraction of passageway 15 by walls 13 while the patient breathes) may be operative to deform first expander component section 166a).

Additionally or alternatively, as shown between FIGS. 6 and 7, expander subassembly 160 may be configured such that, in a particular inflated state (e.g., of FIGS. 3 and 5-7 (e.g., with a fixed particular amount of fluid within passageway 167)), when walls of patient 1 may expand away from expander subassembly 160 or otherwise increase the cross-sectional dimension DW or any other suitable cross-sectional dimension of passageway 15 (e.g., in the direction of arrows CR of FIG. 7), first expander component section 166a may be operative to at least partially inflate (e.g., re-inflate) by receiving fluid from within a portion of passageway 167 of third expander component section 166c to within a portion of passageway 167 of first expander component section 166a (e.g., in the direction of arrows FR of FIG. 7 (e.g., via a portion of passageway 167 of second expander component section 166b and/or via passageway 119 and two or more different openings 106)), thereby re-inflating first expander component section 166a and increasing its cross-sectional dimension EDA back to that of the equilibrium of assembly 100 of FIGS. 3 and 5. Therefore, while expander subassembly 160 may be configured to have an equilibrium geometry of FIGS. 3 and 5 and 7 when a particular amount of fluid is held within expander passageway 167 for a particular expanded state of assembly 100 (e.g., when no external forces are applied to assembly 100 (e.g., by patient 1)), expander subassembly 160 may also be configured to adjust its geometry (e.g., from the adjusted geometry of FIG. 6 back to an equilibrium geometry of FIG. 7) when the amount of fluid held within expander passageway 167 remains the same but when an external force is removed from (e.g., terminated from being applied to) assembly 100 (e.g., when expansion forces in the direction of arrows CR by patient 1 remove or terminate the application of a force on first expander component section 166a by patient 1) and may force fluid from one portion of passageway 167 to another portion of passageway 167 (e.g., by forcing fluid to pass from within a portion of passageway 167 of third expander component section 166c to within a portion of passageway 167 of first expander component section 166a (e.g., in the direction of arrows FR of FIG. 7)). Such an adjustment of the geometry of a particular expanded state of assembly 100 between that of FIG. 6 and that of FIG. 7 may maintain a relationship between assembly 100 and patient 1 for maintaining assembly 100 at the functional position within patient 1 (e.g., maintain a larger cross-sectional dimension of third expander component section 166c within target space 95 than that of opening 19/91 to prevent end 109 of assembly 100 from being inadvertently removed from target space 95) and/or to prevent patient wall injury (e.g., esophageal wall injury). Such expansion and contraction of dimension DW of patient 1 may be due to peristalsis of the esophagus or any other suitable portion of patient 1 that may routinely occur during any suitable procedure using assembly 100. By configuring at least a portion of expander subassembly 160 to deflect or contract or compress or deflate inwardly and rebound outwardly in tandem with expansion and contraction forces of opposing walls of patient 1 about expander subassembly 160, expander subassembly 160 may be enabled to safely interact with patient 1 during use of assembly 100. In some embodiments, the volume of first expander component section 166a may be the same as or less than the volume of third expander component section 166c when assembly 100 is in its equilibrium geometry of a particular expanded state (e.g., of FIGS. 3, 5, and 7). In some particular embodiments, assembly 100 may be configured such that the volume of first expander component section 166a may be less than the volume of third expander component section 166c when assembly 100 is in its equilibrium geometry of a particular expanded state. Additionally or alternatively, assembly 100 may be configured such that the entirety of, or substantially the entirety of, or at least half of, or less than half of but at least some of the volume of fluid within the portion of expander passageway 167 of first expander component section 166a when assembly 100 is in its equilibrium geometry of a particular expanded state may be transferred to within the portion of expander passageway 167 of third expander component section 166c or any other portion of assembly 100 when the equilibrium geometry of the particular expanded state is deformed to a deformed geometry of the particular expanded state (e.g., the deformed geometry of FIG. 6 (e.g., when an external force is applied to expander component 164 (e.g., by patient 1))) without expander subassembly 160 being damaged (e.g., popping or rupturing or deforming such that it cannot return to its equilibrium geometry when external forces are removed). Therefore, at least some or all of the fluid within the portion of expander passageway 167 of first expander component section 166a when assembly 100 is in its equilibrium geometry of a particular expanded state may safely be combined with all of the fluid within the portion of expander passageway 167 of third expander component section 166c when assembly 100 is in its equilibrium geometry of the particular expanded state and held within the portion of expander passageway 167 of third expander component section 166c when assembly 100 is in a deformed geometry of the particular expanded state. In some embodiments, expander subassembly 160 may be inflated to its equilibrium expanded state of FIG. 5 yet with each one of component sections 166a, 166b, and 166c positioned at least partially within target space 95 and then assembly 100 may be pulled in the direction of arrow R such that expander subassembly 160 may be positioned with respect to patient 1 as shown in FIG. 5 (e.g., such movement of assembly 100 from an equilibrium expanded state of subassembly 160 within target space 95 to an equilibrium expanded state of subassembly 160 with first component section 166a outside of target space 95 but in passageway 15 may involve expander subassembly 160 deforming to a deformed expanded state while first component section 166a passes through opening 91 (e.g., similar to the deformation between FIGS. 5, 6, and 7)). Therefore, subassembly 160 may be provided with at least two expandable reservoirs that may be operative to communicate fluid therebetween, such that a first reservoir may receive fluid from and then expel fluid back into a second reservoir such that the communicated fluid may enable the second reservoir to contract and expand (e.g., breath) in concert with walls of a patient that may be in contact with the second reservoir.

Figure 8:
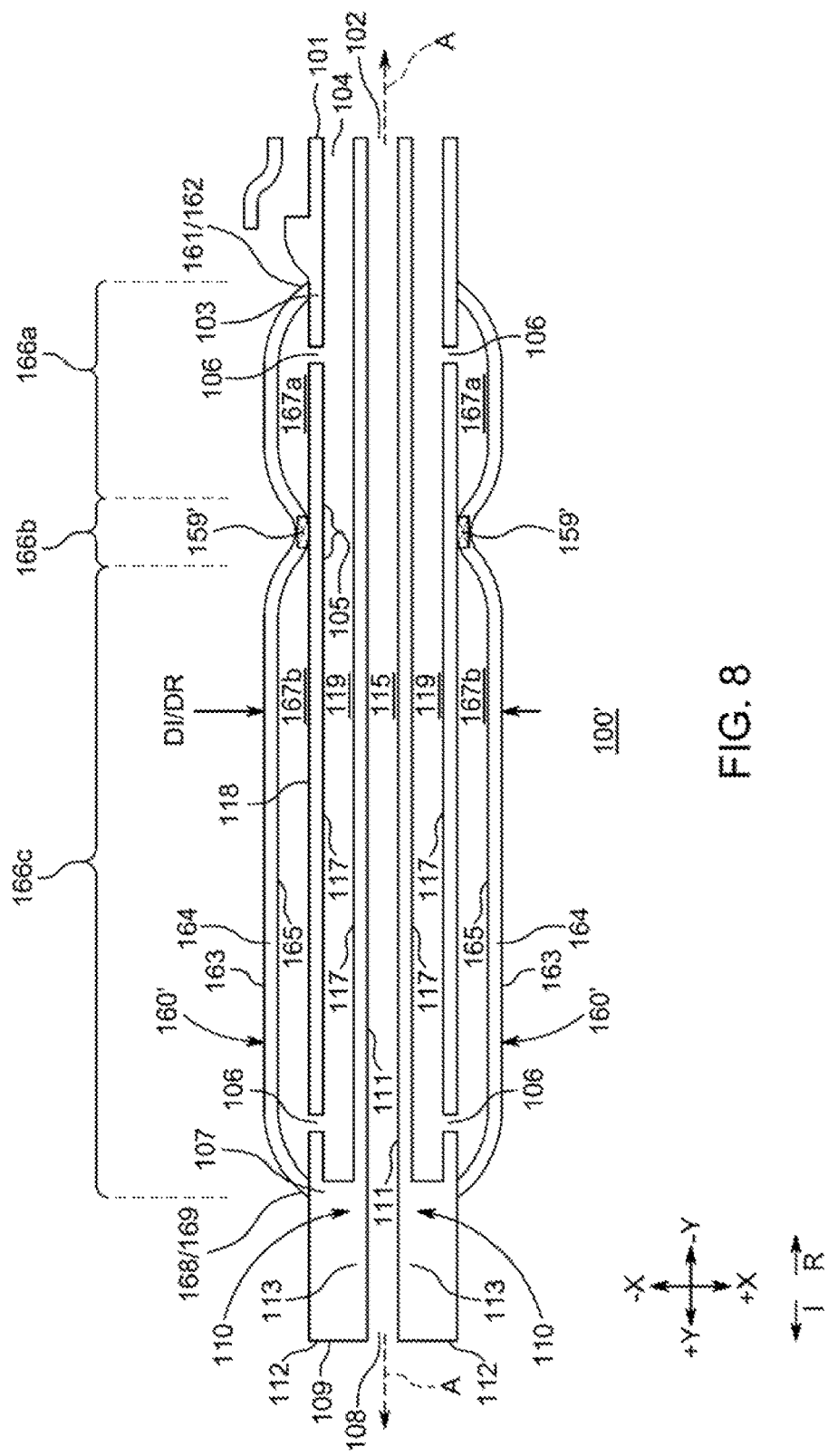
FIG. 8 is a side elevational view of another intubation assembly in an insertion state.
Figure 9:
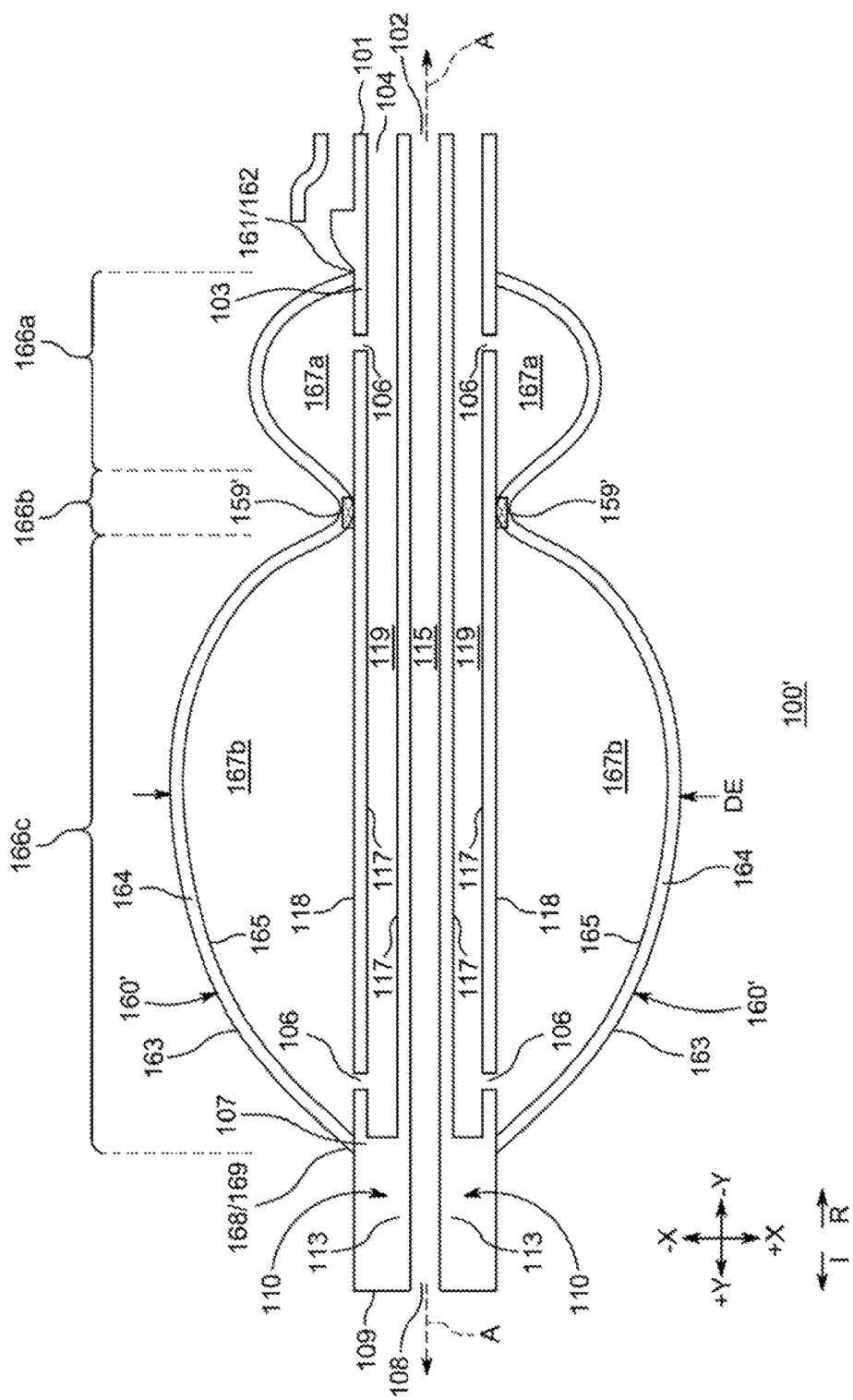
FIG. 9 is a cross-sectional view of the intubation assembly of FIG. 8 in an equilibrium geometry of an expanded state.

As mentioned, second expander component section 166b of assembly 100 of FIGS. 2-7 may be prevented from expanding at all or at least beyond a particular dimension of its equilibrium geometry due to the structural composition of expander component 164 and/or due to any suitable limiting mechanism 159 of assembly 100. Alternatively, as shown in FIGS. 8 and 9, an expander subassembly 160' of an assembly 100', which may otherwise be similar to assembly 100 of FIGS. 2-7, may include any suitable limiting mechanism 159' (e.g., adhesive, molding (e.g., blow molding), crimping, etc.) that may physically couple (e.g., seal) a portion of expander component 164 (e.g., at least a portion or the entirety of second expander component section 166b) to a portion of section 105 along tube subassembly 110, which may split expander passageway 167 into at least two distinct expander sub-passageways 167a and 167b that may be fluidly coupled via two or more openings 106 and passageway 119 but not via another sub-passageway of passageway 167 (e.g., not through limiting mechanism 159'). Alternatively, one or more elements of limiting mechanism 159' may be operative to secure ends of two distinct expander components 164 to a portion of section 105 along tube subassembly 110 (e.g., passageway 167a may be defined by a first expander component and passageway 167b may be defined by a second expander component that may be distinct from the first expander component (e.g., two distinct balloons may be coupled to and about and along different portions of tube subassembly 110)). This may enable the dimension(s) of second expander component section 166b to remain the same or substantially the same as the dimension (s) of section 105 along tube subassembly 110 (e.g., to allow for opening 19/91 to be in its natural state without undue interference from an expandable second expander component section 166b). Similarly, expander component 164 of assembly 100 may be provided by two or more distinct expander components 164 (e.g., first expander component section 166a may be distinct from third expander component section 166c).

Figure 10:
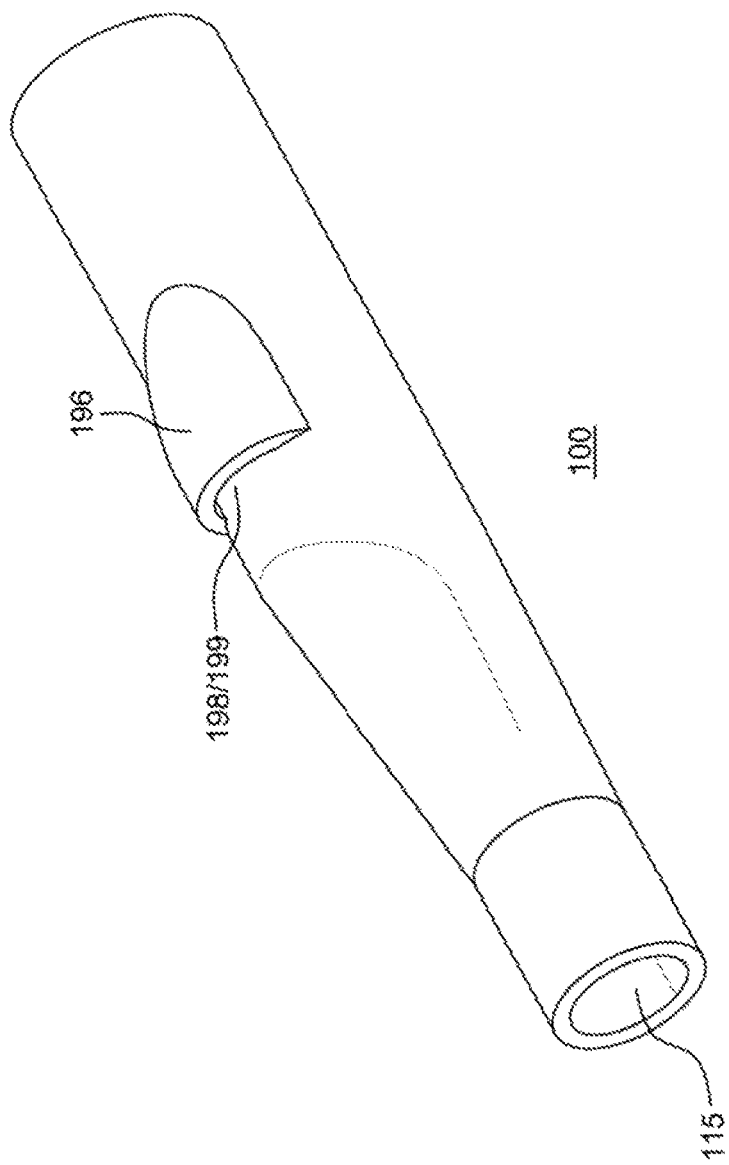
FIGS. 10 and 11 are different perspective views of a portion of the intubation assembly of FIGS. 2-7.
Figure 11:
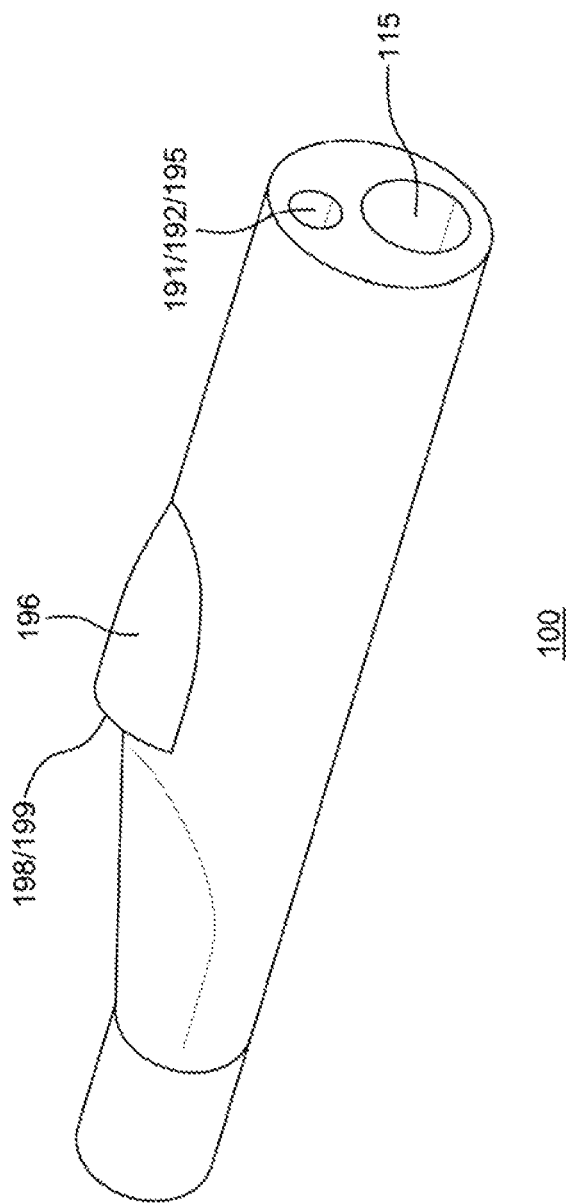
Figure 12:
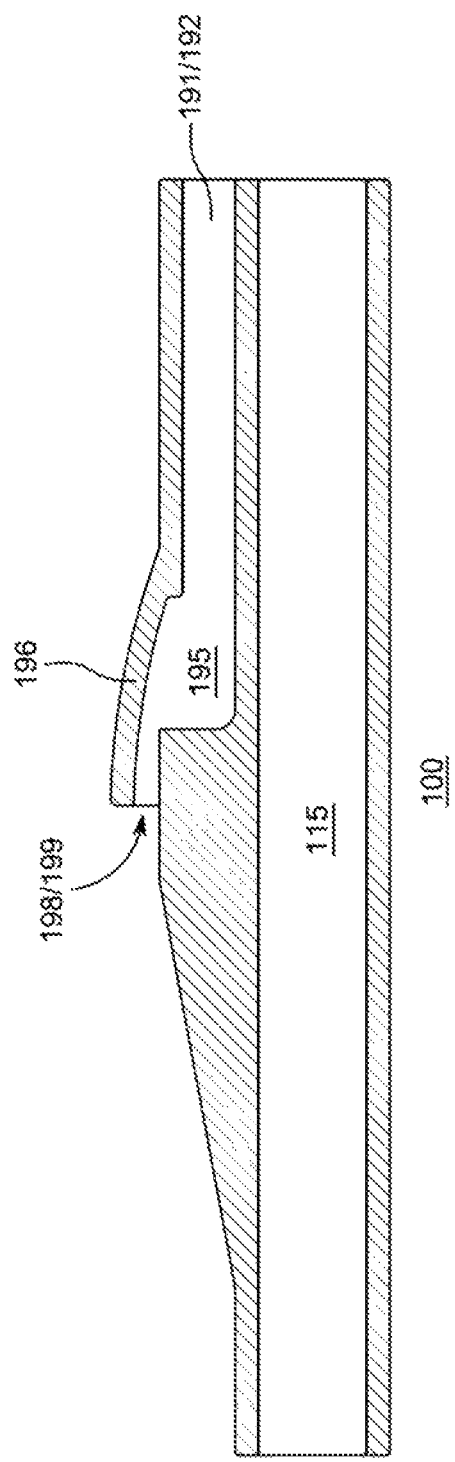
FIG. 12 is a cross-sectional view of the portion of the intubation assembly of FIGS. 10 and 11.
Figure 13:
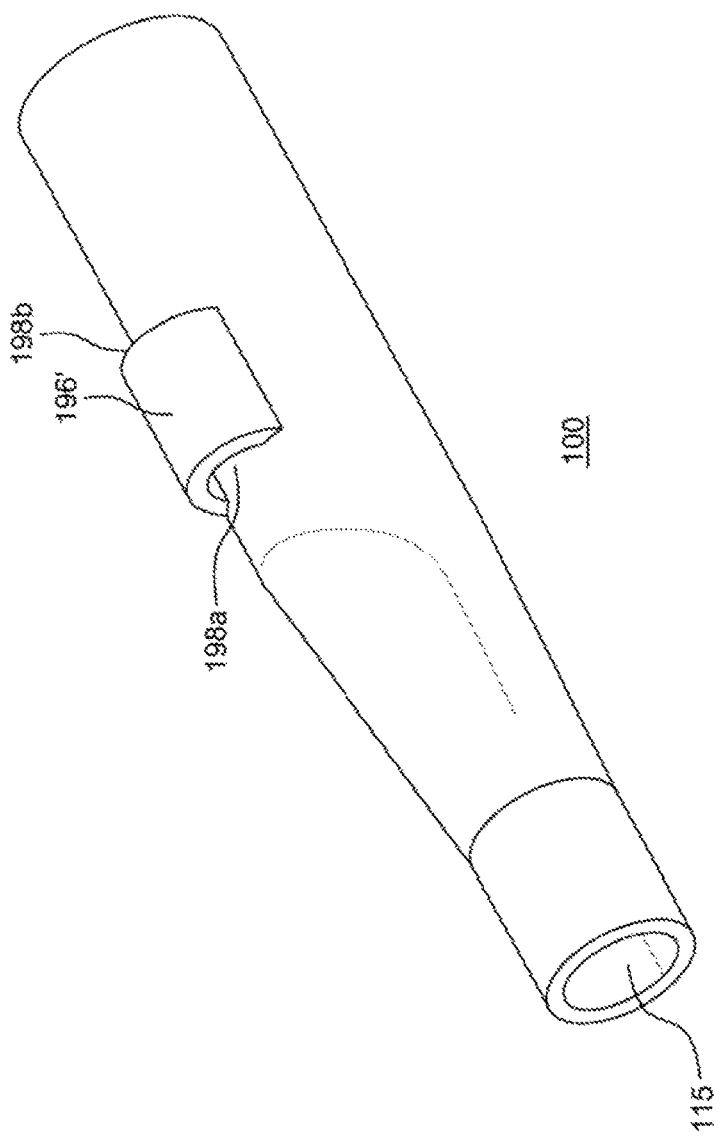
FIGS. 13 and 14 are different perspective views of an alternative portion of the intubation assembly of FIGS. 2-7.
Figure 14:
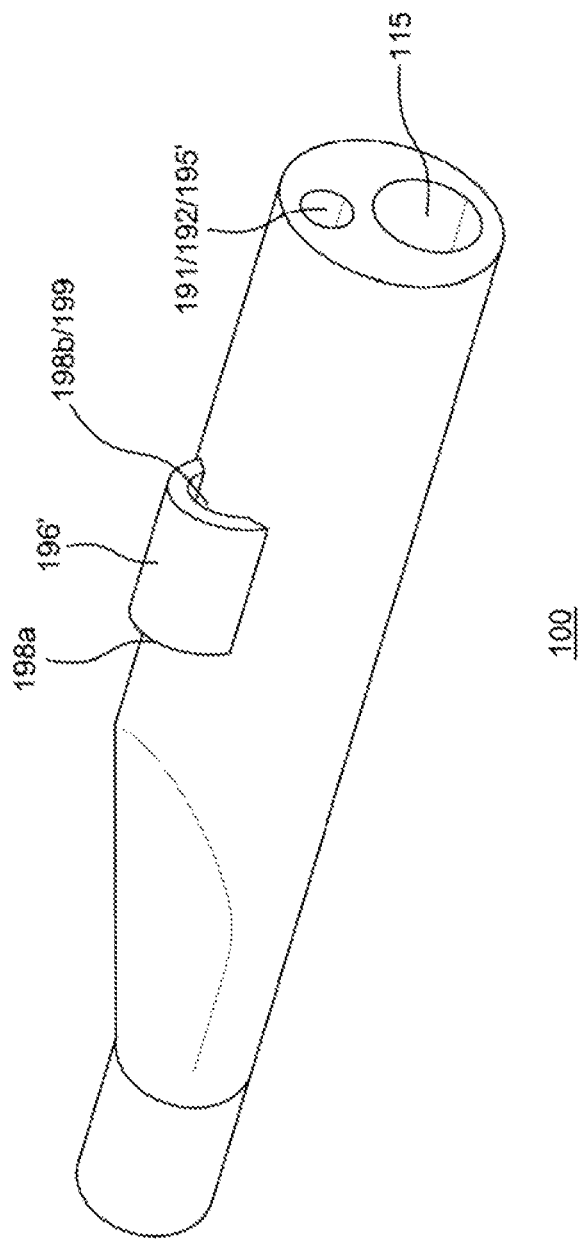
Figure 15:
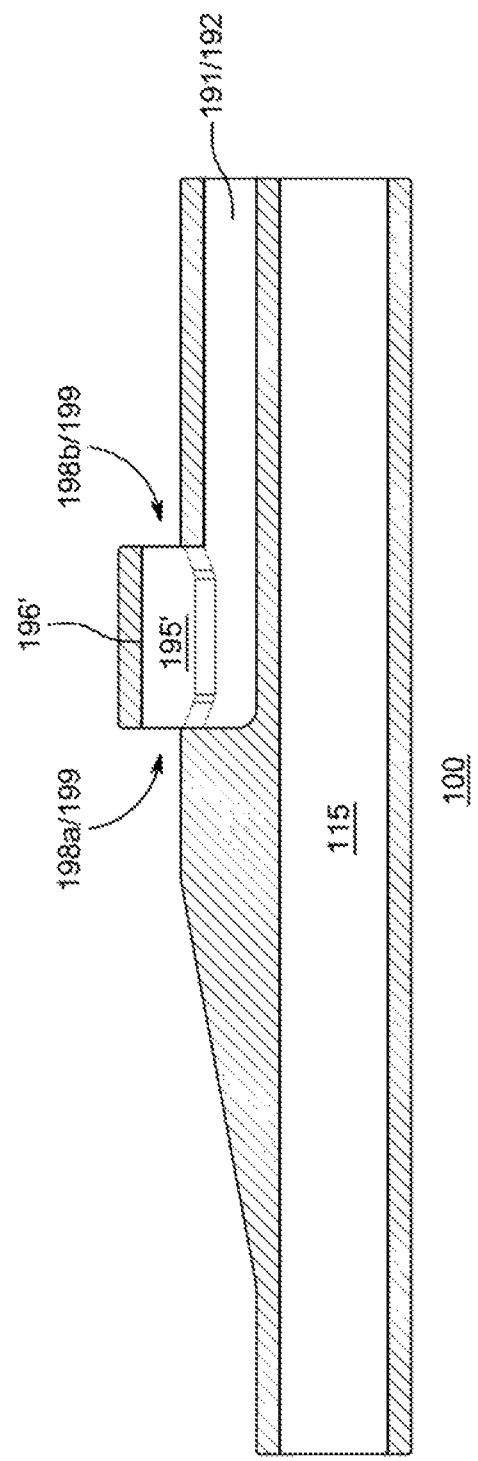
FIG. 15 is a cross-sectional view of the portion of the intubation assembly of FIGS. 13 and 14.

In some embodiments, as shown, for example, in FIGS. 2-3, assembly 100 may also include a supplemental tube passageway 195 that may be defined by at least a portion of one or more walls 113 of tube subassembly 110 that may be provided to treat (e.g., extract material from and/or inject material into) a supplemental region of patient 1 that may be proximal to target 95 and proximal to expander subassembly 160 when assembly 100 is in its expanded state in a functional position within patient 1 (e.g., the position of FIGS. 5-7). For example, as shown, supplemental tube passageway 195 may extend from a proximal end 191 to at least one distal end 199. A proximal opening 192 for passageway 195 may be provided at or near proximal end 191 and a distal opening 198 for passageway 195 may be provided at or near distal end 199. Fluid may be injected into patient 1 (e.g., by operator O) through passageway 195 from opening 192 to opening 198 and/or fluid may be removed from patient 1 (e.g., by operator O) through passageway 195 from opening 198 to opening 192. As shown, at least a portion of passageway 195 may be provided adjacent to passageway 119 and/or passageway 115. As shown in FIGS. 10-12 (without expander passageway 119 (only for simplifying FIGS. 10-12)), an external surface 196 of a wall defining at least a portion of supplemental tube passageway 195 may protrude out from a portion of surface 118 to expose opening 198 at end 199 in a direction facing the direction of expander subassembly 160 (e.g., in direction of arrow I of FIG. 3 for insertion of assembly 100 into a patient), where such a configuration of surface 196 may prevent direct contact between opening 198 and a wall 13 of patient 1 (e.g., to prevent direct suction on a wall of patient tissue) but instead surface 196 may contact patient 1 in certain situations of use while enabling an opening for fluid communication between supplemental tube passageway 195 and passageway 15 of patient 1 (e.g., in a direction along the axis of assembly 100). Alternatively, as shown in FIGS. 13-15 (without expander passageway 119 (only for simplifying FIGS. 13-15)), an external surface 196' of a wall defining at least a portion of a supplemental tube passageway 195' may protrude out from a portion of surface 118 to expose a first opening 198a at end 199 in a direction facing the direction of expander subassembly 160 (e.g., in direction of arrow I for insertion of assembly 100 into a patient, similar to opening 198 of FIGS. 10-12) as well as a second opening 198b at end 199 in a direction substantially opposite of first opening 198a (e.g., in direction of arrow R for removal of assembly 100 into a patient), where such a configuration of surface 196' may prevent direct contact between each opening 198 and a wall 13 of patient 1 (e.g., to prevent direct suction on a wall of patient tissue) but instead surface 196 may contact patient 1 in certain situations of use while enabling multiple openings for fluid communication between supplemental tube passageway 195' and passageway 15 of patient 1 (e.g., up and down along the axis of assembly 100).

Various materials may be used for various elements of an assembly 100, which may vary based on the procedure and/or patient in which assembly 100 is to be used. As just one example, when assembly 100 may be used for a nasogastric intubation procedure, tube subassembly 110 may be made of polyurethane, silicone, polyvinyl chloride, or rubber, expander subassembly 160 may be a molded piece and/or extruded piece and/or may be made of silicone, polyurethane, rubber, thermoplastic elastomers, or the like and/or may be coupled to tube subassembly 110 via any suitable type of mechanism or crimp or bond or adhesive (e.g., cyanoacrylate or silicone glue). One or more of any or all portions of expander subassembly 160 and tube subassembly 110, and/or the like of assembly 100 may be provided with an alkaline coating on one or both of its interior and exterior walls, such that when material (e.g., food or acidic stomach contents) travels through such components, the acidity of the material may get neutralized. Additionally or alternatively, one or more of any or all portions of expander subassembly 160 and tube subassembly 110, and/or the like of assembly 100 may be at least partially X-ray visible such that an operator may ensure that it is properly placed within patient 1 for a particular procedure.

Assembly 100 may be used to treat a patient in any suitable manner. In some embodiments, while expander subassembly 160 may be in a natural or relaxed or un-inflated state (e.g., while the geometry of expander 164 may be similar to the geometry of surface 118 of structure 112), distal end 109 of assembly 100 may be initially inserted into patient 1 and fed through passageway 15, through openings 19/91, and into target space 95. The length of assembly 100 necessary to enable distal end 109 to be positioned within space 95 while proximal end 101 may be accessible to an operator may vary based on the size of patient 1. When a particular length (e.g., 65 centimeters) of assembly 100 has been inserted (e.g., in the direction of arrow I) for a given patient such that an operator may believe distal end 109 is within or close to space 95, or at any other suitable moment, the operator may attempt to determine the location of expander 164 with respect to space 95. In some embodiments, an initial volume of fluid may be injected into passageway 167 via passageway 119 for expanding a portion of passageway 167 to better differentiate the geometry of at least a portion of expander 164 from the geometry of structure 112, and then any suitable technique may be used to detect the location of expander 164 within patient 1. For example, one or more of any or all portions of expander subassembly 160 or tube subassembly 110 may be at least partially X-ray visible (e.g., using a Barium marker dye on a portion of expander 164) such that an operator may ensure that it is properly placed within patient 1 for a particular procedure. This technique may be used even when expander subassembly 160 may be in a natural or relaxed or un-inflated state. The operator may detect the location of expander 164 and further insert assembly 100 into patient 100 until expander 164 is at least partially positioned within space 95. In some embodiments, the operator may position the entirety of expander 164 within space 95. Once expander is at least partially positioned within space 95, a volume of fluid may be injected into passageway 167 via passageway 119 for expanding at least a portion of passageway 167. In some embodiments, an amount of fluid may be injected into and retained within passageways 119 and 167 for expanding a portion of passageway 167 defined by first expander component section 166a and for expanding a portion of passageway 167 defined by third expander component section 166c (e.g., to the state of FIG. 3). In some embodiments, this inflation may occur while each one of expander component sections 166a-166c are within space 95. Then, while the injected fluid is maintained within passageways 119 and 167, assembly 100 may be retracted in the direction of arrow R for pulling at least first expander component section 166a through openings 19/91 and into passageway 15 (e.g., to the position of FIG. 5). This process of pulling inflated first expander component section 166a through openings 19/91 may cause fluid to be temporarily removed from first expander component section 166a and into another portion of passageway 167, such as into expander component section 166c (e.g., as similarly described above with respect to FIG. 6), such that the geometry of expander component section 166a may be squashed or deformed when pulled through openings 19/91. Then, when passed through openings 19/91 and positioned within passageway 15, that fluid may return to first expander component section 166a (e.g., as similarly described above with respect to FIG. 7). Completion of retraction of expander component section 166a through openings 19/91 may be felt by the operator. This retraction of a portion of inflated expander 164 through openings 19/91 in the direction of arrow R may ensure that proximal expander component section 166a and distal expander component section 166c are properly positioned on opposite sides of openings 19/91 (e.g., respectively, in passageway 15 and space 95). Any attempt to further retract assembly 100 may be met by resistance from inflated expander component section 166c against wall 93 of space 95 about opening 91 (e.g., indicating that distal expander component section 116c within space 95 is abutting the gastro esophageal junction).

FIG. 16 is a flowchart of an illustrative process 1600 for intubating a patient with an intubation assembly, wherein the intubation assembly includes a body structure, an intubation passageway extending within the body structure and along at least an intubation portion of the length of the body structure from a proximal intubation passageway opening to a distal intubation passageway opening, an expander subassembly coupled to the body structure for defining an expander passageway between the expander subassembly and the body structure, and an inflation passageway extending along at least an inflation portion of the length of the body structure from a proximal inflation passageway opening to a distal inflation passageway opening, wherein the distal inflation passageway opening fluidly couples the inflation passageway to the expander passageway, wherein the expander subassembly includes a proximal expander subassembly portion defining a proximal portion of the expander passageway between the proximal expander subassembly portion and a proximal portion of the body structure and a distal expander subassembly portion defining a distal portion of the expander passageway between the distal expander subassembly portion and a distal portion of the body structure, wherein the distal inflation passageway opening fluidly couples the inflation passageway to the distal portion of the expander passageway, wherein the inflation passageway further includes an intermediate inflation passageway opening that fluidly couples the inflation passageway to the proximal portion of the expander passageway, and wherein the proximal portion of the expander passageway is fluidly coupled to the distal portion of the expander passageway only via the inflation passageway. At operation 1602 of process 1600, the expander subassembly may be positioned within the patient. For example, as described above and shown in FIG. 1, an assembly 100, which may include expander 160 coupled to tube subassembly 110 of FIGS. 2-9, may be positioned within patient 1. At operation 1604 of process 1600, while the expander subassembly is positioned within the patient, a volume of fluid may be provided within the combined space defined by the inflation passageway and the expander passageway, wherein the providing expands each one of the proximal portion of the expander passageway and the distal portion of the expander passageway, and at operation 1606 of process 1600, the volume of the fluid may be retained within the combined space. For example, as described with respect to FIGS. 1A, 3, and 5, fluid may be injected into and retained within passageway 167 via passageway 119 for expanding a portion of passageway 167 defined by first expander component section 166*a* and for expanding a portion of passageway 167 defined by third expander component section 166*c*. At operation 1608 of process 1600, while the volume of the fluid is retained within the combined space, other fluid may be passed through the intubation passageway for treating the patient. For example, as described with respect to FIGS. 1A-1C, fluid may be passed through passageway 115 for treating patient 1.

It is understood that the operations shown in process 1600 of FIG. 16 are merely illustrative and that existing operations may be modified or omitted, additional operations may be added, and the order of certain operations may be altered.

While there have been described expandable assemblies and methods for using and making the same, it is to be understood that many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. It is also to be understood that various directional and orientational terms such as "proximal" and "distal," "up" and "down," "front" and "back," "top" and "bottom" and "side," "length" and "width" and "thickness" and "diameter" and "cross-section" and "longitudinal," "X-" and "Y-" and "Z-," and the like that may be used herein only for convenience, and that no fixed or absolute directional or orientational limitations are intended by the use of these words. For example, the assemblies and patients can have any desired orientations. If reoriented, different directional or orientational terms may need to be used in their description, but that will not alter their fundamental nature as within the scope and spirit of the subject matter described herein in any way.

Therefore, those skilled in the art will appreciate that the invention can be practiced by other than the described embodiments, which are presented for purposes of illustration rather than of limitation.

What is claimed is:

1. An intubation assembly comprising:
   a body structure extending from a proximal body end to a distal body end;
   an intubation passageway extending within the body structure and along at least an intubation portion of the length of the body structure from a proximal intubation passageway opening to a distal intubation passageway opening;
   an expander subassembly coupled to the body structure for defining an expander passageway between the expander subassembly and the body structure; and
   an inflation passageway extending along at least an inflation portion of the length of the body structure from a proximal inflation passageway opening to a distal inflation passageway opening, wherein:
   the distal inflation passageway opening fluidly couples the inflation passageway to the expander passageway;
   the expander subassembly comprises:
     a proximal expander subassembly portion defining a proximal portion of the expander passageway between the proximal expander subassembly portion and a proximal portion of the body structure; and
     a distal expander subassembly portion defining a distal portion of the expander passageway between the distal expander subassembly portion and a distal portion of the body structure;
   the proximal portion of the expander passageway is fluidly coupled to the distal portion of the expander passageway; and
   when a volume of fluid is retained within the combined space defined by the inflation passageway and the expander passageway:
     a portion of the volume of the fluid is transferred from the proximal portion of the expander passageway to the distal portion of the expander passageway when an external force is applied to the proximal expander subassembly portion; and
     the portion of the volume of the fluid is transferred from the distal portion of the expander passageway to the proximal portion of the expander passageway when the external force is removed from the proximal expander subassembly portion.

2. The intubation assembly of claim 1, wherein the expander subassembly further comprises an intermediate expander subassembly portion defining an intermediate portion of the expander passageway between the intermediate expander subassembly portion and an intermediate portion of the body structure.

3. The intubation assembly of claim 2, wherein the intermediate portion of the expander passageway fluidly couples the proximal portion of the expander passageway to the distal portion of the expander passageway.

4. The intubation assembly of claim 3, wherein the inflation passageway also fluidly couples the proximal portion of the expander passageway to the distal portion of the expander passageway.

5. The intubation assembly of claim 3, wherein the inflation passageway does not fluidly couple the proximal portion of the expander passageway to the distal portion of the expander passageway.

6. The intubation assembly of claim 2, wherein the proximal expander subassembly portion, the intermediate expander subassembly portion, and the distal expander subassembly portion are all provided by a single expander component.

7. The intubation assembly of claim 6, wherein the expander component comprises a balloon.

8. The intubation assembly of claim 2, wherein, when the volume of fluid is retained within the combined space defined by the inflation passageway and the expander passageway, another portion of the volume of the fluid is maintained within the intermediate portion of the expander passageway when the external force is applied to the proximal expander subassembly portion.

9. The intubation assembly of claim 8, wherein, when the volume of fluid is retained within the combined space defined by the inflation passageway and the expander passageway, the other portion of the volume of the fluid is maintained within the intermediate portion of the expander passageway when the external force is not applied to the proximal expander subassembly portion.

10. The intubation assembly of claim 2, further comprising a mechanism positioned about at least a portion of the intermediate expander subassembly portion and operative to prevent the intermediate expander subassembly portion from expanding beyond a certain amount.

11. The intubation assembly of claim 1, wherein:
the distal inflation passageway opening fluidly couples the inflation passageway to the distal portion of the expander passageway; and
the inflation passageway further comprises an intermediate inflation passageway opening that fluidly couples the inflation passageway to the proximal portion of the expander passageway.

12. The intubation assembly of claim 11, wherein the proximal portion of the expander passageway is fluidly coupled to the distal portion of the expander passageway only via the inflation passageway.

13. The intubation assembly of claim 11, wherein:
the proximal expander subassembly portion comprises a proximal expander component extending between a first proximal expander component end coupled about the body structure at a first position along the length of the body structure and a second proximal expander component end coupled about the body structure at a second position along the length of the body structure;
the proximal expander component defines the proximal portion of the expander passageway between the proximal expander component and the proximal portion of the body structure;
the distal expander subassembly portion comprises a distal expander component extending between a first distal expander component end coupled about the body structure at a third position along the length of the body structure and a second distal expander component end coupled about the body structure at a fourth position along the length of the body structure; and
the distal expander component defines the distal portion of the expander passageway between the distal expander component and the distal portion of the body structure.

14. The intubation assembly of claim 13, wherein:
the proximal expander component comprises a first balloon; and
the distal expander component comprises a second balloon that is different than the first balloon.

15. The intubation assembly of claim 14, wherein the proximal portion of the expander passageway is fluidly coupled to the distal portion of the expander passageway only via the inflation passageway.

16. The intubation assembly of claim 1, wherein at least a portion of the inflation passageway extends within the body structure.

17. A method of intubating a patient with an intubation assembly comprising a body structure, an intubation passageway extending within the body structure and along at least an intubation portion of the length of the body structure from a proximal intubation passageway opening to a distal intubation passageway opening, an expander subassembly coupled to the body structure for defining an expander passageway between the expander subassembly and the body structure, and an inflation passageway extending along at least an inflation portion of the length of the body structure from a proximal inflation passageway opening to a distal inflation passageway opening, wherein the distal inflation passageway opening fluidly couples the inflation passageway to the expander passageway, wherein the expander subassembly comprises a proximal expander subassembly portion defining a proximal portion of the expander passageway between the proximal expander subassembly portion and a proximal portion of the body structure and a distal expander subassembly portion defining a distal portion of the expander passageway between the distal expander subassembly portion and a distal portion of the body structure, wherein the distal inflation passageway opening fluidly couples the inflation passageway to the distal portion of the expander passageway, wherein the inflation passageway further comprises an intermediate inflation passageway opening that fluidly couples the inflation passageway to the proximal portion of the expander passageway, and wherein the proximal portion of the expander passageway is fluidly coupled to the distal portion of the expander passageway only via the inflation passageway, the method comprising:
positioning the expander subassembly within the patient;
while the expander subassembly is positioned within the patient:
providing a volume of fluid within the combined space defined by the inflation passageway and the expander passageway, wherein the providing expands each one of the proximal portion of the expander passageway and the distal portion of the expander passageway;
retaining the volume of the fluid within the combined space; and
while the volume of the fluid is retained within the combined space, passing other fluid through the intubation passageway for treating the patient; and
while the volume of the fluid is retained within the combined space:
transferring at least a portion of the volume of the fluid from the proximal portion of the expander passageway to the distal portion of the expander passageway when an external force is applied to the proximal expander subassembly portion; and
transferring the at least a portion of the volume of the fluid from the distal portion of the expander passageway to the proximal portion of the expander passageway when the external force is removed from the proximal expander subassembly portion.

* * * * *